United States Patent [19]

Della Valle et al.

[11] Patent Number: 4,736,024

[45] Date of Patent: Apr. 5, 1988

[54] PROCESS FOR PREPARING SALT OF HYALURONIC ACID WITH A PHARMACEUTICALLY ACTIVE SUBSTANCE

[75] Inventors: Francesco Della Valle, Padova; Aurelio Romeo, Rome; Silvana Lorenzi, Padova, all of Italy

[73] Assignee: Fidia, S.p.A., Abano Terme, Italy

[21] Appl. No.: 847,632

[22] Filed: Apr. 3, 1986

Related U.S. Application Data

[63] Continuation-in-part of Ser. No. 756,824, Jul. 19, 1985.

[30] Foreign Application Priority Data

Apr. 5, 1985 [IT] Italy .............................. 47924 A/85
Dec. 23, 1985 [IT] Italy .............................. 48980 A/85

[51] Int. Cl.$^4$ .............................................. C07M 1/00
[52] U.S. Cl. ................................. 536/55.3; 536/18.7; 536/55.2; 536/54; 536/101; 536/121
[58] Field of Search ................ 536/54, 55.3, 55.2, 536/18.7, 101, 121

[56] References Cited

U.S. PATENT DOCUMENTS

| | | |
|---|---|---|
| 2,583,096 | 1/1952 | Hadidian et al. |
| 3,792,164 | 0/0000 | Bechtold .............................. 514/54 |
| 3,936,081 | 8/1968 | Billek . |
| 4,105,760 | 8/1978 | Szejtli et al. ........................ 514/34 |
| 4,141,973 | 2/1979 | Balaz .................................. 514/54 |
| 4,141,973 | 0/0000 | Balazx ................................. 514/54 |
| 4,303,676 | 12/1981 | Balazs . |
| 4,359,458 | 11/1982 | Naro et al. ........................... 514/54 |

FOREIGN PATENT DOCUMENTS 2099826 of 0000 United Kingdom .
818336 of 0000 United Kingdom .
138572 of 0000 European Pat. Off. .

OTHER PUBLICATIONS

Chem. & Mol. Biol. of the Intercellular Matrix, vol. 2, 1970, pp. 703–732.
Popovica et al. *Chemical Abstracts*, vol. 77, 1972 No. 594m.
Chemical Abstracts, vol. 87, No. 21, Nov. 21, 1977, p. 170, No. 163114a.
Chemical Abstracts, vol. 102, No. 16, Apr. 22, 1985, p. 359, Ref. No. 137591n.
Chemical Abstracts, vol. 68, No. 7, Feb. 12, 1968, p. 2627, Ref. No. 27273g.
Chemical Abstracts, vol. 80, No. 15, Apr. 15, 1974, p. 137, Ref. No. 79756j.
Chemistry and Industry, Feb. 12, 1955, pp. 168–169, Scott.

*Primary Examiner*—J. R. Brown
*Assistant Examiner*—Elli Peselve
*Attorney, Agent, or Firm*—Birch, Stewart, Kolasch & Birch

[57] ABSTRACT

Pharmaceutical preparations for topical administration containing a pharmacologically active substance together with hyaluronic acid or a molecular weight fraction thereof. The hyaluronic acid may be in the form of the free acid or may be a salt with an alkali or alkaline earth metal, magnesium, aluminum or ammonium, or in the form of a salt with one or more pharmacologically active substances.

15 Claims, No Drawings

PROCESS FOR PREPARING SALT OF HYALURONIC ACID WITH A PHARMACEUTICALLY ACTIVE SUBSTANCE

This application is a continuation-in-part of co-pending application Ser. No. 756,824, filed July 19, 1985.

BACKGROUND AND FIELD OF THE INVENTION

The present invention relates to new medicaments for topical use and more precisely it concerns medicaments containing:

1. an active pharmacological substance or a mixture of pharmacological substances, either active or suitable for topical administration and
2. a vehicle which comprises hyaluronic acid or a molecular fraction of hyaluronic acid or a salt of the same with an alkaline metal, an alkaline earth metal, magnesium, aluminium, ammonium or a pharmacological substance, optionally together with additional conventional excipients for pharmaceutical preparations for topical use. The invention further relates to the use of such medicaments for therapeutic or preventive purposes.

The application of a topically active medicament may be a benefit or remedy, especially in dermatology, diseases of the mucuous membranes in general and particularly membranes of the oral and nasal cavities, diseases of the outer ear, and especially diseases of the outer surface of the eye. Application of these topical medicaments is particularly advisable in pediatrics and in the veterinary field.

The advantages of therapy using the medicaments according to the present invention are due to a more efficient vehicle for the drugs promoted by the acidic polysaccharide of the hyaluronic acid component and to a better bioavailability of the active substance as compared to that obtainable with known pharmaceutical formulations. Furthermore, the new medicaments of the invention assume particular importance in the case of ophthalmic medicaments, because due to the above mentioned qualities, there is an additional special compatibility with the corneal epithelium and, therefore, a very high level of tolerability, with no sensitization effects. When the medicaments are administered in the form of concentrated solutions with elastic-viscose characteristics or in solid form, it is possible to obtain films on the corneal epithelium which are homogeneous, stable, perfectly transparent, and which adhere well, quaranteeing prolonged bioavailability of the drug, thereby forming excellent preparations with a retard effect.

Such ophthalmic medicaments are of exceptional value especially in the veterinary field, considering for example that there are at present no veterinary specialities for oculistic use containing chemotherapeutics. Indeed, preparations intended for human use are usually used, and these do not always guarantee a specific range of activity nor comply with the particular conditions in which the treatment should be effected.

This is the case, for example, in therapy for infectious keratoconjunctivitis, pink eye or IBK, an infection which mainly affects cattle, sheep and goats. Presumably, these three species have in common specific etiological factors. In particular, in cattle the main microorganism involved seems to be *Moraxella bovis* (even though other agents of a viral origin should not be excluded, such as *Rhinotracheitis virus,* Micoplasma, Rickettsia and Chlamydia in the case of sheep, and Rickettsia in the case of goats). The disease manifests itself in an acute form and tends to spread quickly. In the initial stages the symptomatology is characterized by blepharospasm and excessive lacrimation, followed by purulent exudate, conjuctivitis and keratitis, often accompanied by fever, reduced apetite and milk production. Lesions of the cornea are particularly serious and in the final stages can even cause perforations of the cornea itself. The clinical course varies from a few days to several weeks.

A vast range of chemotherapeutic agents are used for treatment, administered both topically (often in association with anti-inflammatory steroids), and systemically. Among these are the following: tetracyclines, such as oxytetracycline, penicillins, such as cloxacillin and benzylpenicillin, sulfamides, polymyxin B (associated with miconazole and prednisolone), chloramphenicol, tylosin and chloromycetin. Topical treatment of the disease, despite its apparent simplicity, still represents an unsolved problem, since for one reason or another it has proved impossible up until now to obtain oculistic preparations having concentrations of antibiotics or sulfamides which are therapeutically effective in the secretion of tears. This is quite understandable in the case of solutions, bearing in mind the mainly reclining position of the head in these animals. But it is also true of semisolid medicaments, since the excipients normally used in them do not have the qualities necessary for adhering to the surface of the cornea, as they do not usually have a sufficiently high concentration of active substance and cannot achieve perfect distribution (i.e., the presence of a distribution gradient). These defects of conventional colliriums in ophthalmic use have been described by Slatter et al. in "Austr. vet. J.," 1982, 59 (3), pp. 66–72.

DETAILED DESCRIPTION OF THE INVENTION

One advantage of the present invention is having perfected new types of collirium in which the above defects have been overcome. The use of hyaluronic acid as a vehicle for ophthalmic drugs allows for the formulation of excellent preparations free from concentration gradients of the active substance and, therefore, perfectly homogenous, transparent and adhesive to the corneal epithelium, without sensitization effects, with excellent vehicling of the active substance and possibly with a retard effect.

The above mentioned properties of the new medicaments may of course be used also in other fields besides ophthalmology. As already mentioned, they may be applied in dermatology and in diseases affecting the mucous membranes, such as in the mouth, for instance in odontology. They may also be used to obtain a systemic effect due to the effect of transcutaneous riabsorption, for instance in suppositories. All of these applications are possible both in human and veterinary medicine. In human medicine the new medicaments are particularly suitable for use in pediatrics. The present invention also includes, in particular, any one of the therapeutic applications.

The present invention, therefore, is in its essential aspect related to the use of hyaluronic acid as a vehicle in association with a pharmaceutical substance to provide an improved drug delivery system. New medicaments according to the invention basically contain two components:

Component (1)—a pharmaceutically active substance, including, as discussed below, mixtures of different such substances.

Component (2)—hyaluronic acid, including as discussed below, molecular weight fractions of hyaluronic acid and various salts of hyaluronic acid or the molecular weight fractions thereof.

The present invention can further be characterized as including physical mixtures of Component (1) and Component (2), complexes of the Component (1) active substance with the Component (2) hyaluronic acid, or various combinations or mixtures thereof.

COMPONENT (1)—PHARMACEUTICAL SUBSTANCE

The Component (1) may first of all be catagorized with respect to its use in the various fields of therapy, starting with the distinction between human and veterinary medicine and then specifying the various sectors of application with respect to the organs or to the tissues to be treated, such as ophthalmology, dermatology, otorhinolaryngology, obstetrics, angiology, neurology or any type of pathology of the internal organs which may be topically treated, such as for example rectal applications. According to a particular aspect of the present invention, the pharmacologically active substance (1) is first and foremost for ophthalmic use. According to another criterion, the pharmacologically active substance (1) must be distinct with respect to its effect and may therefore, for example, be used as an anesthetic, analgesic, vasoconstrictor, antibacterial, antiviral, or anti-inflammatory agent. For the ophthalmic field, it may particularly be indicated for example for its miotic, anti-inflammatory, wound healing and antimicrobial effects.

The component (1) may also be, according to the invention, a mixture of two or more active substances. For example, in ophthalmology, an antibiotic may be associated with an antiphlogistic and a vasoconstrictor or several antibiotics may be associated with one or more antiphlogistics, or one or more antibiotics may be associated with a mydiatric, a miotic, a wound healing or an antiallergic agent. For example it is possible to use the following associations of ophthalmic drugs: (a) kanamycin+phenylephrine+phosphate dexamethasone; (b) kanamycin+phosphate betamethasone+phenylephrine, or similar associations with other antibiotics used in ophthalmology, such as rolitetracycline, neomycin, gentamicin, and tetracycline.

In dermatology it is possible to use as the active component (1) or mixtures of various antibiotics, such as erythromycin, gentamicin, neomycin, gramicidin, polymyxin B, or mixtures of such antibiotics with anti-inflammatory agents, for example corticosteroids. For example, mixtures comprising: (a) hydrocortisone+neomycin; (b) hydrocortisone+neomycin+polymyxin B+gramicidin; (c) dexamethasone+neomycin; (d) fluorometholon+neomycin; (e) prednisolone+neomycin; (f) triamcinolone+neomycin+gramicidin+nistatine, or any other mixture used in conventional preparations for dermatology. The mixtures of various active substances are not of course limited to this field, but in each of the above mentioned fields of medicine it is possible to use mixtures similar to those already in use for the known pharmaceutical preparations of the art.

Examples of the pharmacologically active substance (1) for use in ophthalmic medicaments according to the invention are: basic and non-basic antibiotics, for example aminoglucosidics, macrolides, tetracycline and peptides, such as for example gentamicin, neomycin, streptomycin, dihydrostreptomycin, kanamycin, amikacina, tobramycin, spectinomycin, erythromycin, oleadomycin, carbomycin, spiramycin, oxytetracycline, rolitetracycline, bacitracin, polymyxin B, gramicidin, colistin, chloramphenicol, lincomycin, vancomycin, novobiocin, ristocetin, clindamycin, amphotericin B, griseofulvin, nystatin and possibly their salts, such as sulphates or nitrates, or mixtures of the same or with other active principles, such as those mentioned hereafter.

Other ophthalmic drugs to be used to advantage according to the present invention are: other anti-infective agents such as diethylcarbamazine, mebendazole, sulfamides such as sulfacetamide, sulfadiazine, sulfisoxazole; antiviral and antitumor agents such as iododeoxyuridine, adenine arabinoside, trifluorothtmidine, aciclovir, ethyldeoxyuridine, bromovinyldeoxyuridine, 5-iodo-5'-amino-2',5'-dideoxyuridine; steroid anti-inflammatory agents, such as for example dexamethasone, hydrocortisone, prednisolone, fluorometholon, medrysone and possibly their esters, for example esters of phosphoric acid; non-steroid anti-inflammatory agents, for example indomethacin, oxyphenbutazone, flurbiprofen; wound healers such as the epidermal growth factor EGF; local anesthetics, such as Benoxinate, proparacaine and possibly their salts; cholinergic agonist (promoter) drugs such as pilocarpine, metacholine, carbaylocholine, aceclidine, physiostigmine, neostigmine, demecarium and possibly their salts; cholinergic antagonist drugs such as atropine and its salts; the adrenergic agonist (promoter) drugs such as noradrenaline, adrenaline, naphozoline, methoxamine and possibly their salts; and adrenergic antagonist drugs such as propanolol, timolol, pindolol, bupranolol, atenolol, metoprolol, pindolol, bupranolol, atenolol, metoprolol, oxprenolol, practolol, butoxamine, sotalol, budarine, labetalol and possibly their salts.

As noted above, the active Component (1) may take the form of a mixture to two or more active substances. Examples of active substances to be used alone or in mixture between themselves or with other active principles in dermatology are: therapeutic agents such as anti-infective, antibiotic, antimicrobial, anti-inflammatory, cytostatic, cytotoxic, antiviral, anesthetic agents, and prophylactic agents, such as sun shields, deodorants, antiseptics and disinfectants. Of the antibiotics the following should be noted: erythromycin, bacitracin, gentamicin, neomycin, aureomycin, gramicidin and their mixtures, of the antibacterials and disinfectants: nitrofurazone, mafenide, chlorhexidine, and derivatives of 8-hydroxyquinoline and possibly their salts; of the anti-inflammatory agents, above all the corticosteroids such as prednisolone, dexamethasone, flumethasone, clobetasol, triamcinolone acetonide, betamethasone or their esters, such as valerianates, benzoates, dipropionates; of the cytotoxics, bluorouracil, methotrexate, podophyllin; of the anesthetics dibucaine, lidocaine, benzocaine.

The list is of course only for illustrative purposes and any other agent described in literature may be used.

Of the examples mentioned for ophthalmology and dermatology, it is possible to conclude by analogy which are the medicaments according to the present invention to be used in the above mentioned fields of medicine, such as for example in otorhinolaryngology or odontology or in internal medicine, for example in endocrinology, where it is possible to effect treatments with preparations for intradermic absorption or absorption through the mucous, for example rectal or intranasal absorption, for example such as nasal sprays or inhalations in the oral cavity and in the pharynx.

These preparations may therefore be for example anti-inflammatory, or vasoconstricting or vasopressors such as those already mentioned for ophthalmology, vitamins, antibiotics, such as those mentioned above, hormones, chemiotherapeutics, antibacterials, etc., including those mentioned above for use in dermatology.

COMPONENT (2)—HYALURONIC ACID VEHICLE

As noted above, the medicaments of the invention comprise as Component (2) hyaluronic acid, molecular weight fractions thereof, or various salts thereof. Hyaluronic acid (hereinafter sometimes referred to a "HY") is a natural heteropolysaccharide which is composed of alternating residues of D-glucuronic acid and N-acetyl-D-glucosamine. HY is present in pericellular gels, in the fundamental extracellular substance of connective tissues, in vertabrate organisms, in the synovial fluid of the joints, in the vitreous humor, in human umbellical tissue, in cocks' combs and in some bacteria. Its molecular weight is about 8–13 million.

The first research carried out on HY was by Balazs (see U.S. Pat. No. 4,141,973), who isolated a HY fraction able to substitute for endobulbar fluids and suitable for other therapeutic applications. Hyaluronic acid and its molecular weight fractions with lower molecular weights have in fact proved widely useful in medicine and a cosmetic use is also being considered (see for example, Balazs et al., Cosmetics & Toiletries, Italian Edition No. 5/84). It has especially been used as a therapeutic agent in therapies for arthropathies, such as in the veterinary field to cure arthritis in horses (Acta Vet. Scand. 167, 379 (1976).

Hyaluronic acid and its molecular fractions have been used in ophthalmic surgery as therapeutic, auxilliary and substitutive agents for natural organs and tissues (see for example E. A. Balazs et al., Modern Problems in Ophthalmology, 10, 3 (1970), E. B. Strieff, S. Karger, eds. Basel and Balazs et al., Viscosurgery and the Use of Sodium Hyaluronate During Intraocular Lens Implantation, Paper presented at the International Congress and First Film Festival on Intraocular Implantation, Cannes, 1979).

In published European patent application No. 0138572 filed on Oct. 10, 1984, there is a description of a molecular fraction of hyaluronic acid which may be used for intraocular and intra-articular injections, respectively, suitable for the substitution of the endobulbar fluids in the eye and for therapy of arthropathies.

In contrast to this therapeutic use or as a plastic auxiliary in surgery or in cosmetics, in the present invention, hyaluronic acid or its molecular fractions are used as vehicles for the administration of pharmacologically active substances for topical use.

As a vehicle to be used as the component (2) of the present invention, hyaluronic acid of any origin may be used, such as the acids extracted from the above mentioned natural starting materials, including cocks' combs. The preparation of crude extracts of such acids is described in literature. Preferably, purified hyaluronic acids should be used. According to the invention, in the place of integral hyaluronic acids obtained directly be extraction of the organic materials, it is possible to use fractions of the same with molecular weights which may vary greatly, such as for example from about 90–80% (MW=11.7–10.4 million) to 0.23% (MW=30,000) of the molecular weight of an integral acid having a molecular weight of 13 million, preferably between 5% and 0.23%. Such fractions may be obtained by various procedures such as by hydrolyzing, oxydizing or enzymatic chemical agents, physical procedures such as mechanical or by irradiation, and, therefore, are often formed in the same purification procedures of the primary extracts (see for example, Balazs et al., Cosmetics and Toiletries, cited above). The separation and purification of the fractions obtained is achieved, for example, by molecular filtration.

Of particular importance to be utilized as the vehicle (2) according to the present invention are two purified fractions which may be obtained from hyaluronic acid, for example from cocks' combs, and known as Hyalastine and Hyalectin. The fraction known as Hyalastine has an average molecular weight of about 50,000 and 100,000. Hyalectin has an average molecular weight of about 500,000 to 730,000. A combined fraction of these two fractions has also been isolated and characterized as having an average molecular weight of about 250,000 to about 350,000. This combined fraction may be obtained with a yield of 80% of total hyaluronic acid available from the particular starting material, while the fraction Hyalectin may be obtained with a yield of 30% and the fraction Hyalastine wih a yield of 50% of the starting HY. (The preparation of these fractions is described in Examples 20–22, hereinafter).

Thus, the preferred hyaluronic acid to be utilized is a molecular weight fraction having a molecular weight broadly ranging from about 30,000 to about 13 million and preferably from about 30,000 to about 730,000. The most preferred hyaluronic fractions have a molecular weight of from about 50,000 to about 100,000, or from about 500,000 to about 730,000, or a combined fraction having a molecular weight of from 250,000 to about 350,000. These preferred fractions are importantly substantially free of low molecular weight hyaluronic acid having a molecular weight of less than about 30,000, and, therefore, are free of inflammatory side reactions when administered. (Further references hereinafter to hyaluronic acid or HY are intended to include, where consistent with the particular context, both hyaluronic acid and molecular weight fractions thereof.)

According to the invention, in place of hyaluronic acids and their molecular weight fractions as the Component (2) of the medicaments, it is also possible to use their salts with inorganic bases, such as alkali metal (sodium, potassium, lithium), alkali earth metal (calcium, barium, strontium), magnesium or aluminum. These salts may be stoichiometrically neutral in the sense that all the acid functions are salified, or partial salts or acids, in which only a certain number of the acid functions are salified with the above mentioned metals. Such salts are easily obtained, for example, by reacting HY or the above mentioned fractions with the basic calculated quantity, and it is also possible to use mixed salts originating from different bases.

In addition to the above salts, it is also possible to utilize salts of HY with compounds which can broadly be considered ammonium or substituted ammonium (amines), for example mono, di, tri and tetra-alkylammonium where the alkyl groups have preferably between 1 and 18 carbon atoms or arylalkyls with the same number of carbon atoms in the aliphatic portion and where aryl means a benzene residue, optionally substituted with between 1 and 3 methyl, halogen, or hydroxy groups. These ammonium or substituted ammonium salts of HY are formed by chemical reaction between hyaluronic acid and primary, secondary or tertiary amine moieties or ammonium hydroxide moieties of compounds or drugs having pharmaceutical activity, that is, with these moieties of the compounds which comprise active Component (1). As with the above-discussed salts, these salts also may be stoichiometrically neutral wherein all of the acid functions are salified, or may be partial salts or acids, and may comprise mixed salts originating from different bases.

Hyaluronic acid or its molecular fractions as the Component (2) may, therefore, be substituted by their salts with inorganic bases, such as alkali metal (sodium, potassium, lithium), alkaline earth metal (calcium, barium, strontium), magnesium, aluminum, ammonium or substituted ammonium. This principal is also valid for the above mentioned partial acid salts, in which all the acid groups present may be partially or totally neutralized with the above mentioned metals, or with ammonia or with amines, wherein the ammonium salts are formed by chemical reaction between hyaluronic acid and primary, secondary or tertiary amine moieties or ammonium hydroxide moieties of compounds or drugs having pharmaceutical activity, i.e. Component (1).

MEDICAMENT PREPARATIONS COMBINING COMPONENTS (1) AND (2)

There are various possibilities of realizing the medicaments according to the invention including:

(a) using a neutral or acid active substance Component (1) mixed together with hyaluronic acid or a molecular weight fraction thereof, or their metallic salts;

(b) using partial salts of HY with a basic active substance Component (1) leaving the residual acid groups of HY free or neutralized with the above-mentioned metals or bases;

(c) using stoichiometrically neutral salts of HY with a basic substance Component (1), possibly adding HY or one of its partial or total (neutral) metal salts;

(d) using stoichiometrically neutral salts of HY with a basic substance Component (1), adding further quantities of Component (1); and (e) using ad libitum mixtures of the salts or of the mixtures described hereinabove.

One particular form of medicament according to the invention is represented by mixtures of the pharmacologically active substance Component (1) with hyaluronic acids or molecular fractions thereof when the said active substance (1) is of a basic nature, for example in the case of basic antibiotics. In this case, the hyaluronic acid component (2) and the active substance (1) together from stoichiometrically partial salts, or acid salts, in which an aliquot part of all the acid groups of the HY Component (2) are salified with the basic groups of the active Component (1); or stoichiometrically neutral salts, in which all the groups of the HY Component (2) are salified, or mixtures of these neutral salts with a further quantity of the basic active substance (1).

Therefore, for the purpose of the present invention, if a basic active substance (1) is used, it is possible to replace the mixtures of Components (1) and (2) with the above mentioned acid salts or those which are stoichiometrically neutral, or, of course mixtures of such salts both with Component (1) and with Component (2).

Mixtures of drugs between themselves and possibly with other principles may also be used as the active Component (1) according to the invention. If, in the place of only one active substance (1), mixtures of active substances are used, such as those mentioned above, the salts of the basic active substances and hyaluronic acid and its molecular weight fractions may be mixed salts of one or more of such basic substances or possibly mixed salts of this type with a certain number of other acid groups of the HY polysaccharide salified with the above mentioned metals or bases. For example, it is possible to prepare salts of hyaluronic acid or one of the molecular fractions Hyalastine or Hyalectin with a certain percentage of salified acid groups with the antibiotic kanamycin, another percentage salified with the vasocostrictor phenylephrine, while a remaining percentage acid groups are free or salified for example with sodium or another of the above mentioned metals. It is also possible to mix this type of mixed salt with other quantities of hyaluronic acid or its fractions or their metallic salts, as indicated above for the medicament containing salts of only one active substance with the aforesaid acidic polysaccharides.

It is, therefore, possible according to a particular aspect of the present invention to use the above mentioned salts, isolated and possibly purified to the solid anhydrous state, as an amorphous powder. When the powder comes into contact with the tissue to be treated, the powder forms a concentrated aqueous solution of a gelatinous character, of a viscous consistency, and with elastic properties. These qualities are also maintained at stronger dilutions and may therefore be used in place of the above mentioned anhydrous salts, solutions in water at various degrees of concentration or in saline, possibly with the addition of other pharmaceutically acceptable excipients or additives, such as other mineral salts to regulate the pH and the osmotic pressure. It is also possible of course to use the salts to make gels, inserts, creams or ointments, in which there are other excipients or ingredients used in conventional formulations of these pharmaceutical preparations. According to a particular aspect of the invention, there is a preference for the medicaments containing hyaluronic acid, the molecular weight fractions thereof or their mineral salts or their partial or neutral salts with the active substance (1) as the sole vehicle (with the possible exception of an aqueous solvent).

The quantitative ratios by weight of the two components (1) and (2) according to the invention may vary within ample limits and this naturally depends also on the nature of the two components and in the first case on that of the active substance. Such limits are for example the ratios of 0.01:1 and 100:1 between the two components (1) and (2). The range of variation however is preferably between the limits of 0.01:1 and 10:1 for the two said components and especially between 0.1:1 and 2:1.

The medicaments according to the invention may be in solid form, for example freeze-dried powders containing only the two components in mixture or separately packed.

In solid form, such medicaments form, on contact with the epithelium to be treated, more or less concentrated solutions according to the nature of the particular epithelium with the same characteristics of the previously prepared solutions in vitro which represent another particularly important aspect of the present invention. Such solutions are preferably in distilled water or sterile saline and contain preferalby no other pharmaceutical vehicle besides hyaluronic acid or one of its salts. The concentrations of such solutions may also vary within ample limits, for example between 0.01 and 75% both for each of the two components taken separately, and for their mixtures or salts. There is a particular preference for solutions of a pronounced elastic-viscose character, for example with a content of between 10% and 90% of the medicament or of each of its components. Medicaments of this type are particularly important, both in an anhydrous form (freeze-dried powders) or concentrated solutions or diluted in water or saline, possibly with the addition of additive or auxiliary substances, such as particular disinfectant substances or mineral salts acting as buffer or others, for ophthalmic use.

Among the medicaments of the invention the following should be chosen in particular, as the case may be, those with a degree of acidity suiting the place to which they are to be applied, that is with a physiologically tolerable pH. Adjustment of the pH, for example in the above mentioned salts of hyaluronic acid with a basic active substance, may be effected by regulating in a suitable manner the quantities of polysaccharide, of its salts and of the basic substance itself. Thus, for example, should the acidity of a hyaluronic acid salt with a basic substance be too high, the excess of the free acid groups with the above mentioned inorganic bases is neutralized, for example with sodium or potassium or ammonium hydrate.

The following formulations are exemplary of preparations according to the present invention comprising an association of an active pharmaceutical Component (1) and the vehicle Component (2) comprising hyaluronic acid.

Formulation 1—A GEL CONTAINING EGF OF WHICH 100 g CONTAIN:
HY sodium salt (Hyalastine fraction), 55 g
HY sodium salt (Hyalectin fraction), 30 g
EGF 0.5 g
twice distilled water 23.5 g Formulation 2—A 100 mg INSERT WITH PILOCARPINE NITRATE CONTAINING:
HY sodium salt (Hyalastine fraction), 100 mg
Pilocarpine nitrate, 2 mg Formulation 3—A POWDER FORM FOR TOPICAL APPLICATION CONTAINING STREPTOMYCIN:
100 g of powder contain:
HY sodium salt (Hyalastine fraction), 70 g
HY sodium salt (Hyalectin fraction), 28.5 g
Streptomycin 1.5 g Formulation 4—A 100 mg INSERT WITH PILOCARPINE CONTAINING:
mixed salt of hyaluronic acid with pilocarpine and with sodium (see preparation in Example 18, 100 mg Formulation 5—A COLLIRIUM CONTAINING GENTAMYCIN AND NAPHAZOLINE, OF WHICH 100 ml CONTAINS:
mixed salt of hyaluronic acid with gentamycin, with naphazoline and with sodium (see preparation in Example 16), 2.910 g
propyl oxybenzoate, 0.050 g
sodium phosphate, 1.500 g
distilled water, q.b.a. 100 ml Formulation 6—A COLLIRIUM WITH CHLORAMPHENICOL, NEOMYCIN, PHENYLEPHRINE, NITROFURAZONE, OF WHICH 100 ml CONTAINS:
mixed salt of hyaluronic acid with neomycin, with phenylephrine and with sodium (see preparation Example 17), 2.890 g
chloramphenicol, 0.500 g
nitrofurazone, 0.02 g
distilled water, q.b.a. 100 ml Formulation 7—A COLLIRIUM WITH DEXAMETASONE PHOSPHATE, KANAMYCIN E PHENYLEPHRINE, OF WHICH 100 ml CONTAINS:
mixed salt of hyaluronic acid with kanamycin and phenylephrine (see preparation Example 15), 3.060 g
dexametasone phosphate sodium salt, 0.100 g
methyl p-hydroxybenzoate, 0.060 g
distilled water, q.b.a. 100 ml.

METHODS OF PREPARATION

Method A

The preparation of the salts according to the invention may be carried out in a known manner by bringing together solutions or suspensions in water or in organic solvents of the two components (1) and (2) and possibly of bases or basic salts of the above mentioned alkali metal, alkali earth metals, magnesium, aluminum or ammonium, in calculated quantities and isolating the salts in an amorphous anhydrous form according to known techniques. It is possible, for example to first prepare aqueous solution of the two components (1) and (2), freeing such components from aqueous solutions of their salts with acids of the metallic salts, respectively, for example, sulphates in the case of component (1) and sodium salts in the case of component (2) for treatment with relative ionic exchangers, uniting the two solutions at a low temperature, for example between 0° and 20°. If the salt thus obtained is easily soluble in water, it should be freeze-dried, while salts which are not easily soluble may be separated by centrifugation, filtration or decantation and possibly then essicated.

The following examples are given merely as illustrative of Method A of the present invention and are note to be considered as limiting.

EXAMPLE 1

PREPARATION OF THE SALT OF HYALURONIC ACID (HY) WITH STREPTOMYCIN 2.43 g of streptomycin sulfate (10 mEq) are solubilized in 25 ml of distilled $H_2O$. The solution is eluted in a thermostatic column at 5° C., containing 15 ml of quaternary ammonium resin (Dowex 1×8) in the $OH^-$ form. The sulfate-free eluate is collected in a thermostatic container at 5° C. 4.0 g of the sodium salt of hyaluronic acid having a molecular weight of 255,000 (corresponding to 10 mEq of a monomeric unit) are solubilized in 400 ml of distilled $H_2O$. The solution is then eluted in a thermostatic column at 5° C., containing 15 ml of sulfonic resin (Dowex 50×8) in the $H^+$ form. The sodium-free eluate is collected under agitation in the solution of streptomycin base. The resulting solution is frozen and instantly freeze-dried. In the salt thus obtain, all of the acidic groups of hyaluronic acid are salified with the basic functions of streptomycin. Yield: 5.5 g.

Microbiological determination on *Bacillus subtilis* ATCC 6633 compared to standard streptomycin shows a content of 33.8% by weight of streptomycin base, corresponding to the theoretically calculated weight.

Colorimetric determination of the glucuronic acid combined in polysaccharide according to the method of Bitter et al. (Anal. Biochem. 4, 330, 1962) shows a content by weight of HY acid of 66.2% (theoretical percentage 66.0%)

EXAMPLE 2

PREPARATION OF THE SALT OF HYALURONIC ACID (HY) WITH ERYTHROMYCINE 4.0 g of the sodium salt of hyaluronic acid with a molecular weight of 77,000 corresponding to 10 mEq of a monomeric unit are solubilized in 400 ml of distilled $H_2O$. The solution is then eluted in a thermostatic column at 5° C., containing 15 ml of sulfonic resin (Dowex 50×8) in the H+ form. The eluate, free from sodium, is kept at a temperature of 5° C. 7.34 g of erythromycin base (10 mEq) are added to the solution of HY under agitation at 5° C. until complete solubilization is obtained. The resulting solution is frozen and freeze-dried. In the salt thus obtain, all of the acid groups of hyaluronic acid are salified with erythromycin. Yield: 10.8 g.

Microbiological determination on staphylococcus aureus ATCC 6538p in comparison with standard erythromycin shows a content of 66.0% by weight of erythromycin base, corresponding to the theoretical value. Colorimetric determination of the glucuronic acid combined in the polysaccharide according to the method of Bitter et al. shows a content of HY acid of 34.0% by weight, corresponding to the theoretically calculated percentage.

EXAMPLE 3

PREPARATION OF THE SALT OF HYALURONIC ACID (HY) WITH KANAMYCIN 1.46 g of dikanamycin sulphate (10 mEq) are solubilized in 25 ml of distilled $H_2O$. The solution is eluted in a thermostatic column at 5° C., containing 15 ml of quaternary ammonium resin (Dowex 1×8) in the OH− form. The eluate, free from sulfates, is gathered in a thermostatic container at 5° C. 4.0 g of the sodium salt of HY having a molecular weight of 165,000 corresponding to 10 mEq of a monomeric unit are solubilized in 400 ml of distilled $H_2O$. The solution is then eluted in a thermostatic column at 5° C., containing 15 ml of sulfonic resin (Dowex 50×8) in the H+ form. The eluate, free from sodium, is collected under vortex agitation in the solution of kanamycin base. The solution thus obtained is instantly frozen and freeze-dried. Yield: 4.8 g.

In the salt obtained, all the acid groups of HY are salified with kanamycin. Microbiological determination on B. subtilis ATCC 6633 in comparison with standard kanamycin shows a content of 24.2% by weight of kanamycin base, corresponding to the theoretically calculated percentage.

Colorimetric determination of the glucuronic acid combined in polysaccharide according to the method of Bitter et al. shows a content of HY acid of 75.8% by weight, also corresponding to the theoretical content.

EXAMPLE 4

PREPARATION OF THE SALT OF HYALURONIC ACID (HY) WITH NEOMYCIN 1.52 g of neomycin sulfate (10 mEq) are solubilized in 20 ml of distilled $H_2O$ and eluted in a thermostatic column at 5° C., containing 15 ml of quatenary ammonium resin (Dowex 1×8) in the OH− form. The eluate, free from sulfates, is collected in a theermostatic container at 5° C. 4.0 g of HY sodium salt with a molecular weight of 170,000 corresponding to 10 mEq of a monomeric unit are solubilized in 400 ml of distilled $H_2O$ and eluted in a thermostatic column at 5° C. containing 15 ml of sulfonic resin (Dowex 50×8) in the H+ form. The eluate, free from sodium, is gathered under agitation in the solution of neomycin base. The viscoelastic precipitate which forms is separated by decantation and freeze-dried. Yield: 4.76 g.

In the resulting salt, all of the HY acid groups are salified with neomycin. Quantitative microbiological determination carried out on S. aureus ATCC 6538p compared to standard neomycin shows a content by weight of 21.2% of neomycin base, corresponding to the theoretically calculated value.

Colorimetric determination of the glucuronic acid combined in polysaccharide according to the metod of Bitter et al. shows a HY acid content of 78.8% by weight.

EXAMPLE 5

PREPARATION OF THE SALT OF HYALURONIC ACID (HY) WITH GENTAMYCIN 1.45 g of gentamycin sulfate (10 mEq) are solubilized in 25 ml of distilled $H_2O$. The solution is eluted in a thermostatic column at 5° C., containing 15 ml of quaternary ammonium resin (Dowex 1×8) in the OH− form. The eluate, free from sulfates, is collected in a thermostatic container at 5° C. 4.0 g of the sodium salt of HY with a molecular weight of 170,000 corresponding to 10 mEq of a monomeric unit are solubilized in 400 ml of distilled $H_2O$. The solution is then eluted in a thermostatic column at 5° C., containing 15 ml of sulfonic resin (Dowex 50×8) in the H+ form. The eluate, free from sodium, is collected under agitation in a vortex in the solution of gentamycin base. The thick and very viscous precipitate which forms is separated by decantation and freeze-dried. Yield: 4.65 g.

In the salt thus obtained, all the HY acid groups are salified with gentamycin. Quantitative microbiological determination carried out on S. epidermidus ATCC 12228 compared to standard gentamycin shows a content by weight of 20.0% of gentamycin base, corresponding to the theoretical content.

Colorimetric determination of the glucuronic acid combined in polysaccharide according to the method of Bitter et al. shows a HY acid content of 80.0%.

EXAMPLE 6

PREPARATION OF THE SALT OF HYALURONIC ACID (HY) WITH AMIKACIN 1.47 g of amikacin base (10 mEq) are solubilized in 100 ml of distilled $H_2O$ at 500° C. 4.0 g of the sodium salt of HY with a molecular weight of 170,000 corresponding to 10 mEq of a monomeric unit are solubilized in 4000 ml of distilled $H_2O$. The solution is then eluted in a thermostatic column at 5° C., containing 15 ml of sulfonic resin (Dowex 50×8) in the H+ form. The eluate, free from sodium, is collected under agitation in a vortex in the solution of amikacin. The thick and extremely viscous precipitate which forms is separated by decantation and freeze-dried. Yield: 5.16 g.

In the salt thus obtained, all the HY acid groups are salified with amikacin. Quantitative microbiological determination carried out on *S. aureus* ATCC 29737 in comparison to standard amikacin shows a content of 27.7% by weight in amikacin base, corresponding to the theoretical content.

Colorimetric determination of the glucuronic acid combined in polysaccharide according to the method of Bitter et al. shows a HY acid content of 72.3% by weight.

EXAMPLE 7

PREPARATION OF THE SALT OF HYALURONIC ACID (HY) WITH ROLITETRACYCLINE 4.0 g of HY sodium salt having a molecular weight of 170,00 corresponding to 10 mEq of a monomeric unit are solubilized in 400 ml of distilled $H_2O$. The solution is then eluted in a thermostatic column at 5° C., containing 15 ml of sulfonic resin (Dowex 50×8) in the H+ form. The eluate, free from sodium, is kept at a temperature of 5° C. 5.3 g of rolitetracycline base (10 mEq) are added to the solution of HY acid under agitation at 5° C. away from the light, until complete solubilization has been achieved. The solution thus obtained is instantly frozen and freeze-dried. Yield: 8.9 g.

In the salt thus obtained, all the HY acid groups are salified with rolitetracycline. Microbiological determination on *B. pumilus* ATCC 14884 in comparison to standard rolitetracycline shows a content of 58.2% by weight of rolitetracycline base, corresponding to the theoretical value. Colorimetric determination of the glucuronic acid combined in polysaccharide according to the method of Bitter et al. shows a HY acid content of 41.8% by weight.

EXAMPLE 8

PREPARATION OF THE SALT OF HYALURONIC ACID (HY) WITH POLYMYXIN B 2.4 g of polymyxin B base (10 mEq) are suspended in 100 ml of distilled $H_2O$ at 5° C. 4.0 g of HY sodium salt with a molecular weight of 170,000 corresponding to 10 mEq of a monomeric unit are solubilized in 400 ml of distilled $H_2O$. The solution is then eluted in a thermostatic column at 5° C., containing 15 ml of sulfonic resin (Dowex 50×8) in the H+ form. The eluate, free from sodium, is collected under vigorous agitation in the suspension of polymyxin base at 5° C. After an initial phase during which the solution becomes clear, there is a progressive formation of a difficultly soluble product which is completely precipitated by 5 volumes of acetone. The precipitate is filtered, washed with acetone and then vacuum dried. Yield: 6.05 g.

In the salt thus obtained, all of HY acid groups are salified with polymyxin B. Quantitative microbiological determination carried out on *B. bronchiseptica* ATCC 4617 in comparison to standard polymyxin B shows a content of 38.7% by weight of polymyxin B. base, corresponding to the theoretical value.

Colorimetric determination of the glucuronic acid combined in polysaccharide according to the method of Bitter et al. shows a HY acid content of 61.3%.

EXAMPLE 9

PREPARATION OF THE SALT OF HYALURONIC ACID (HY) WITH GRAMICIDIN S 6.7 g of gramacidin S hydrochloride salt (10 mEq) are suspended in 200 ml of ethanol/$H_2O$ (80:20). The solution is then eluted in a thermostatic column at 5° C., containing 15 ml of quaternary ammonium resin (Dowex 1×8) in the OH$^-$ form. 4.0 g of the sodium salt of HY with a molecular weight of 165,000 corresponding to 10 mEq of a monomeric unit are solubilized in 400 ml of distilled $H_2O$. The solution is then eluted in a thermostatic column at 5° C., containing 15 ml of sulfonic resin (Dowex 50×8) in the H+ form.

200 ml of dimethyl sulfoxide (DMSO) are added to the eluate, free from sodium, and the mixture is kept under agitation at 5° C. The solution of gramicidin base is then slowly added. The resulting solution is precipitated by 10 volumes of acetone. The precipitate is filtered, washed with acetone and vacuum dried. Yield: 9.55 g.

In the salt thus obtained, all the HY acid groups are salified with gramicidin S. Quantitative microbiological determination carried out on *S. faecium* ATCC 10541 in comparison to standard gramicidin S shows a content of 60.0% by weight of gramicidin S base, corresponding to the theoretical value.

Colorimetric determination of the glucuronic acid combined in polysaccharide according to the method of Bitter et al. shows a HY acid content of 40.0%.

EXAMPLE 10

PREPARATION OF THE SALT OF HYALURONIC ACID (HY) WITH NAPHAZOLINE

Pure naphazoline base is prepared as follows: 4.94 g of naphazoline-HCl (20 mM) are solubilized in 100 ml of distilled $H_2O$ at 5° C. 20 ml of $NH_4OH$ (5M) are added and extracted twice with 100 ml of ethyl acetate. The organic layers are extracted twice with 50 ml of $H_2O$, mixed together again and anhydrified with anhydrous $Na_2SO_4$. The solution is concentrated at about 50 ml and then placed in a freezer to crystallize. The crystallized product is filtered, washed with ethyl acetate and vacuum dried. Yield: 4.0 g of pure naphazoline base.

4.0 g of the HY sodium salt with a molecular weight of 625,000, corresponding to 10 mEq of a monomeric unit, are solubilized in 400 ml of distilled $H_2O$ and eluted in a thermostatic column at 5° C., containing 15 ml of sulfonic resin (Dowex 50×8) in the H+ form. The eluate, free from sodium, is kept at a temperature of 5° C. 2.1 g of naphazoline base (10 mEq) are added to the solution of HY acid and the mixture is agitated at 5° C. until complete solubilization is achieved. The resulting mixture is instantly frozen and freeze-dried. Yield: 5.72 g.

In the salt thus obtained, all the HY acid groups are salified with naphazoline. Quantitative spectrophotometric determination, carried out in comparison to a naphazoline standard (USP) shows a content of 35.7% by weight of naphazoline base, corresponding to the theoretical value.

Colorimetric determination of the glucuronic acid combined in polysaccharide according to the method of Bitter et al. shows a HY acid content of 64.3%.

EXAMPLE 11

PREPARATION OF THE SALT OF HYALURONIC ACID (HY) WITH PHENYLEPHRINE 2.04 g of L-phenylephrine-HCl (10 mEq) are solubilized in 25 ml of distilled H$_2$O. The solution is eluted in a thermostatic column at 5° C., containing 15 ml of quaternary ammonium resin (Dowex 1×8) in the OH$^-$ form. The eluate, free from chlorides, is collected in a thermostatic container at 5° C. 4.0 g of a HY sodium salt having a molecular weight of 820,000 corresponding to 10 mEq of a monomeric unit are solubilized in 400 ml of distilled H$_2$O. The solution is then eluted in a thermostatic column at 5° C., containing 15 ml of sulfonic resin (Dowex 50×8) in the H$^+$ form. The eluate, free from sodium, is collected under agitation in the solution of phenylephrine base. The resulting mixture is instantly frozen and freeze-dried. Yield: 5.25 g.

In the salt thus obtained, all the HY acid groups are salified with phenylephrine. U.V. spectrophotometric determination using the standard addition method (USP) shows a content of 30.6% by weight of phenylephrine base, corresponding to the theoretical content.

Colorimetric determination of the glucuronic acid combined in polysaccharide according to the method of Bitter et al. shows a HY acid content of 69.4%.

EXAMPLE 12

PREPARATION OF THE SALT OF HYALURONIC ACID (HY) WITH ATROPINE 4.0 g of HY sodium salt having a molecular weight of 1,300,000 corresponding to 10 mEq of a monomeric unit are solubilized in 400 ml of distilled H$_2$O. The solution is then eluted in a thermostatic column at 5° C., containing 15 ml of sulfonic resin (Dowex 50×8) in the H$^+$ form. The eluate, free from sodium, is kept at a temperature of 5° C. 2.89 of atropine base (10 mEq) are added to the solution of HY acid and the mixture is agitated at 5° C. The resulting mixture is frozen and freeze-dried. Yield: 6.5 g.

In the salt thus obtained, all the hyaluronic acid groups are salified with atropine. Quantitative gas chromatography determination (USP) carried out in comparison to standard atropine shows a content of 43.3% in atropine base, corresponding to the theoretical value.

Colorimetric determination of the glucuronic acid combined in polysaccharide according to the method of Bitter et al. shows a HY acid content of 56.7%.

EXAMPLE 13

PREPARATION OF THE SALT OF HYALURONIC ACID (HY) WITH PILOCARPINE 2.45 g of pilocarpine hydrochloride (10 mEq) are solubilized in 50 ml of distilled H$_2$O. The solution is eluted in a thermostatic column at 5° C., containing 15 ml of quaternary ammonium resin (Dowex 1×8) in the OH$^-$ form. The eluate, free from chlorides, is collected in a thermostatic container at 5° C. 4.0 g of HY sodium salt with a molecular weight of 170,000 corresponding to 10 mEq of a monomeric unit are solubilized in 400 ml of distilled H$_2$O. The solution is then eluted in a thermostatic column at 5° C., containing 15 ml of sulfonic resin (Dowex 50×8) in the H$^+$ form. The eluate, free from sodium, is collected under agitation in the solution of pilocarpine base. The solution thus obtained is instantly frozen and freeze-dried. Yield: 5.25 g.

In the salt thus obtained, all the HY acid groups are salified with pilocarpine. Spectrophotometric determination according to the USP carried out in comparison to a pilocarpine standard shows a content of 35.1% by weight of pilocarpine base, corresponding to the theoretical value.

Colorimetric determination of the glucuronic acid combined in polysaccharide according to the method of Bitter et al. shows a HY acid content of 64.6%.

EXAMPLE 14

PREPARATION OF THE SALT OF HYALURONIC ACID (HY) WITH NEOMYCIN AND WITH POLYMYXIN 4.0 g of HY sodium salt having a molecular weight of 170,000 corresponding to 10 mEq of a monomeric unit are solubilized in 400 ml of distilled H$_2$O. The solution is eluted in a thermostatic column at 5° C., containing 15 ml of sulfonic resin (Dowex 50×8) in the H$^+$ form. The eluate, free from sodium is collected in a thermostatic container at 5° C. 0.150 g of polymyxin B base (0.63 mEq) are added under vigorous agitation. 1.425 g of neomycin sulphate (9.37 mEq) are solubilized in 25 ml of distilled H$_2$O. The solution is eluted in a thermostatic column at 5° C., containing 15 ml of quaternary ammonium resin (Dowex 1×8) in the OH$^-$ form. The eluate, free from sulphates, is collected under vigorous agitation in the solution of HY acid and polymyxin B. The precipitate which forms is separated by centrifugation and vacuum dried; there is no loss of the product in the residual solution. Yield: 4.85 g.

17.25 mg of this product contains:
Neomycin equal to 5.0 mg of Neomycin sulphate
Polymyxin equal to 0.63 mg (about 5000 UI) of polymyxin sulphate.

These determinations were carried out after separation by HPLC (high pressure liquid chromatography) of the two active principles.

EXAMPLE 15

PREPARATION OF THE MIXED SALT OF HYALURONIC ACID (HY) WITH KANAMYCIN AND WITH PHENYLEPHRINE 4.0 g of HY sodium salt having a molecular weight of 65,000 corresponding to 10 mEq of a monomeric unit are solubilized in 400 ml of distilled H$_2$O. The solution is then eluted in a thermostatic column at 5° C., containing 15 ml of sulfonic resin (Dowex 50×8) in the H$^+$ form. The eluate, free from sodium, is collected in a thermostatic container at 5° C. 0.85 g of kanamycin sulphate (5.82 mEq) are solubilized in 10 ml of distilled H$_2$O. The solution is eluted in a thermostatic column at 5° C., containing 10 ml of quaternary ammonium resin (Dowex 1×8) in the OH$^-$ form.

The eluate, free from sulphates, is collected in a container kept at a temperature of 5° C. The phenylephrine base is prepared by dissolving phenylephrine hydrochloride in distilled H$_2$O at 5° C. at 100 mg/ml, and NH$_4$OH (6N) is added until complete precipitation is achieved. The precipitate is separated by filtration, washed with distilled H$_2$O until the chlorides have disappeared from the washing water, and then vacuum dried. The HY acid and kanamycin base solutions are mixed and kept at a temperature of 5° C. 699 mg of phenylephrine base (4.18 mEq) are added under agitation until being completely dissolved. The resulting solution is frozen and freeze-dried. Yield: 5.1 g.

Microbiological determination on *B. subtilis* ATCC 6633 in comparison to standard kanamycin shows a content of 13.55% by weight of kanamycin base. U.V. spectrophotometric determination using the standard addition method (USP) shows a content of 13.45% by weight of phenylephrine base.

Colorimetric determination of the glucuronic acid combined in polysaccharide according to the method of Bitter et al. shows a HY acid content of 73.0%.

EXAMPLE 16

PREPARATION OF MIXED SALT OF HYALURONIC ACID (HY) WITH GENTAMYCIN, WITH NAPHAZOLINE AND WITH SODIUM 4.0 g of HY sodium salt with a molecular weight of 50,000 corresponding to 10 mEq of a monomeric unit are solubilized in 400 ml of distilled $H_2O$. The solution is then eluted in a thermostatic column at 5° C., containing 15 ml of sulfonic resin (Dowex 50×8) in the $H^+$ form. The eluate, free from sodium, is collected in a thermostatic container at 5° C. 1.245 g of gentamycin sulphate (8.59 mEq) are solubilized in 25 ml of distilled $H_2O$. The solution is eluted in a thermostatic column at 5° C., containing 12 ml of quaternary ammonium resin (Dowex 1×8) in the $OH^-$ form.

The eluate, free from sulphates, is collected in a container kept at a temperature of 5° C. The pure naphazoline base is prepared with naphazoline-hydrochloride dissolved in distilled $H_2$ at 5° C. at a concentration of 50 mg/ml, $NH_4OH$ (5M) is added until pH 12 is achieved and the solution is extracted twice with ethyl acetate. The organic layers are washed with $H_2O$ and anhydrified on anhydrous $Na_2SO_4$. The product is placed in a freezer to crystallize, and the precipitate is filtered, washed with ethyl acetate and vacuum dried. 2.5 g of HY sodium salt and 0.297 g of naphazoline base are added to the HY acid (1.41 mEq) and agitated until being completely solubilized. The solution of gentamycin base is then added, homogenized and then frozen and freeze-dried. Yield: 7.35 g.

Quantitative microbiological determination on *B. epidermidus* ATCC 12228 in comparison to a gentamycin standard shows a content of 11.1% by weight of gentamycin base. Quantitative spectrophotometric determination carried out in comparison to standard naphazoline (USP) shows a content of 4.0% by weight of naphazoline base.

Colorimetric determination of the glucuronic acid combined in polysaccharide according to the method of Bitter et al. shows a HY acid content of 83.0%.

EXAMPLE 17

PREPARATION OF THE MIXED SALT OF HYALURONIC ACID (HY) WITH NEOMYCIN, WITH PHENYLEPHRINE AND WITH SODIUM 4.0 g of HY sodium salt having a molecular weight of 65,000 corresponding to 10 mEq of a monomeric unit are solubilized in 400 ml of distilled $H_2O$. The solution is then eluted in a thermostatic column at 5° C., containing 15 ml of sulfonic resin (Dowex 50×8) in the $H^+$ form. The eluate, free from sodium, is collected in a thermostatic container at 5° C. 1.28 g of neomycin sulphate (8.42 mEq) are solubilized in 25 ml of distilled $H_2O$. The solution is eluted in a thermostatic column at 5° C., containing 12 ml of quaternary ammonium resin (Dowex 1×8) in the $OH^-$ form.

The eluate, free from sulphates, is collected in a container kept at a temperature of 5° C. The phenylephrine base is prepared by dissolving phenylephrine hydrochloride in distilled $H_2O$ at 5° C. at 100 mg/ml, and adding $NH_4OH$ (6N) until complete precipitation is achieved. The precipitate is separated by filtration, washed with distilled $H_2O$ until the chlorides have disappeared from the washing water, and then it is vacuum dried.

2.5 g of HY sodium salt and 0.266 g of phenylephrine base (1.58 mEq) are added to a solution of HY acid and agitated until being completely solubilized. The solution of neomycin base is then added and after homogenization it is frozen and freeze-dried. Yield: 7.35 g.

Spectrophotometric determination by U.V. using the standard addition method (USP) shows a content of 3.57% by weight of phenylephrine base. Quantitative microbiological determination on *B. aureus* ATCC 6538p in comparison to a neomycin standard shows a content of 11.64% by weight of neomycin base.

Colorimetric determination of the glucuronic acid combined in polysaccharide according to the method of Bitter et al. shows a HY acid content of 82.8%.

EXAMPLE 18

PREPARATION OF THE SALT OF HYALURONIC ACID (HY) WITH PILOCARPINE AND WITH SODIUM 98.31 g of HY sodium salt having a molecular weight of 170,000 corresponding to 245 mEq of a monomeric unit are solubilized in 8.5 liters of distilled $H_2O$.

The solution is then eluted in a thermostatic column at 5° C., containing 300 ml of sulfonic resin (Dowex 50×8) in the $H^+$ form. The eluate, free from sodium, is collected in a thermostatic container at 5° C.

2.34 g of pilocarpine hydrochloride (9.6 mEq) are solubilized in 50 ml of distilled $H_2O$. The solution is eluted in a thermostatic column at 5° C., containing 15 ml of quaternary ammonium resin (Dowex 1×8) in the $OH^-$ form.

The eluate, free from chlorides, is collected under agitation in the solution of HY acid. 235.4 ml of a solution of sodium hydroxide (1M) are slowly added under agitation. The solution thus obtained is instantly frozen and freeze-dried. Yield: 99.8 g.

100 mg of the product contains 2 mg of pilocarpine as a base.

EXAMPLE 19

PREPARATION OF THE SALT OF HYALURONIC ACID (HY) WITH STREPTOMYCIN AND WITH SODIUM 98.68 g of HY sodium salt having a molecular weight of 255,000 corresponding to 246 mEq of a monomeric unit are solubilized in 8.5 liters of distilled $H_2O$. The solution is then eluted in a thermostatic column at 5° C., containing 300 ml of sulfonic resin (Dowex 50×8) in the $H^+$ form. The eluate, free from sodium, is collected in a thermostatic container at 5° C.

1.88 g of streptomicin sulphate (7.74 mEq) are solubilized in 20 ml of distilled $H_2O$. The solution is eluted in a thermostatic column at 5° C., containing 12 ml of quaternary ammonium resin (Dowex 1×8) in the $OH^-$ form.

The eluate, free from sulphates, is collected under agitation in the solution of HY acid. 238.3 ml of a solution of NaOH (1M) are slowly added under agitation and the resulting solution is instantly frozen and freeze-dried. Yield: 99.8 g.

100 g of the product contain 1.5 g of streptomicin as a base.

EXAMPLE 20

METHOD TO OBTAIN A MIXTURE OF THE FRACTIONS HYALASTINE AND HYALECTIN WITH NO IMFLAMMATORY ACTIVITY

Fresh or frozen cocks' combs (3000 g) are minced in a meat mincer and then carefully homogenized in a mechanical homogenizer. The paste thus obtained is then treated in a stainless steel container (AISI 316) or in glass with 10 volumes of anhydrous acetone. The whole is then agitated for 6 hours at a speed of 50 rpm. It is left to separate for 12 hours after which the acetone is discarded by siphoning. The acetone extraction is repeated until the discarded acetone reaches the right degree of humidity (Karl-Fischer method). The whole is then centrifuged and vacuum dried at a suitable temperature for 5-8 hours. About 500-600 g of dry powder of cocks' combs are thus obtained.

300 g of dry powder are exposed to enzymatic digestion with papain (0.2 g) under aqueous conditions and buffered with phosphate buffer in the presence of a suitable quantity of cysteine hydrochloride.

The resultant is agitated for 24 hours at 60 rpm, keeping the temperature at 60°-65° C. It is then cooled at 25° C. and Celite ® (60 g) is added, maintaining the agitation for another hour. The mixture thus obtained is filtered until a clear liquid is obtained. The clear liquid then undergoes molecular ultrafiltration using membranes with a molecular weight exclusion limit of 30,000, in order to retain on the membrane those molecules with a molecular weight greater than 30,000.

The product is ultrafiltered from 5 to 6 original volumes, adding distilled water continually to the product during the ultrafiltration procedure. The addition of water is discontinued and the ultrafiltration is continued until the volume is reduced to ⅓ of the original volume. The residual liquid is rendered 0.1M by the addition of sodium chloride and the temperature is brought to 50° C. Under agitation at 60 rpm, 45 g of cetylpyridine chloride are added. The solution is agitated for 60 minutes and then 50 g of Celite ® are added. Under agitation, the temperature of the whole is brought to 25° C. and the precipitate formed by centrifugation is collected. The precipitate obtained is suspended in a 0.01M solution in sodium chloride (5 liters) containing 0.05% of cetylpyridinium chloride. The resulting suspension is agitated for 60 minutes at 50° C.; the temperature is then brought to 25° C. and the precipitate is centrifuged. The washing operation is repeated 3 times after which the precipitate is collected in a container having 3 liters of a 0.05M solution of sodium chloride containing 0.05% of cetylpyridine chloride. It is agitated at 60 rpm for 60 minutes and the temperature is kept constant at 25° C. for two hours. The supernatant is eliminated by centrifugation. The procedure is repeated several times with solutions of 0.1M sodium chloride containing 0.05% of cetylpyridinium chloride. The mixture is centrifuged and the supernatant is discarded. The precipitate is dispersed in a solution of 0.30M sodium chloride containing 0.05% of cetylpyridinium chloride (3 liters). The mixture is agitated and both the precipitate and the clear liquid are collected. Extraction is repeated 3 more times on the precipitate, each time using 0.5 liter of the same aqueous solution.

Finally the precipitate residue is eliminated and the clear liquids are all placed together in a single container. The temperature of the liquid is brought to 50° C. while under constant agitation. The liquid is then brought to 0.23M with sodium chloride. 1 g of cetylpyridinium chloride is added, and the liquid is kept under agitation for 12 hours. The mixture is cooled to 25° C. and then it is filtered first on a Celite ® pack and then through a filter. It then undergoes molecular ultrafiltration again, on a membrane with a molecular weight exclusion limit of 30,000, ultrafiltering three initial volumes with the addition of a solution of 0.33M sodium chloride. The addition of sodium chloride solution is interrupted and the volume is reduced to ¼ of the initial volume. The solution thus concentrated is precipitated under agitation (60 rpm) at 25° C. with 3 volumes of ethanol (95%). The precipitate is collected by centrifugation and the supernatant is discarded. The precipitate is dissolved in 1 liter of a 0.1M solution of sodium chloride and the precipitation is repeated with 3 volumes of ethanol (95%). The precipitate is collected and washed first with ethanol (75%) 3 times, and then with absolute ethanol (3 times), and finally with absolute acetone (3 times). The product thus obtained (Hyalastine+Hyalectin fractions) has an average molecular weight of between 250,000 and 350,000. The HY yield is equal to 0.6% by weight of the original fresh tissue.

EXAMPLE 21

METHOD TO OBTAIN THE FRACTION HYALASTINE FROM THE MIXTURE OBTAINED BY THE METHOD DESCRIBED IN EXAMPLE 20

The mixture obtained by the method described in Example 20 is dissolved in twice distilled, apyrogenetic water at the rate of 10 mg of product to each 1 ml of water. The solution obtained is exposed to molecular filtration through filter membranes with a molecular weight exclusion limit of 200,000, following a concentration technique on the membrane without the addition of water. During the process of ultrafiltration through membranes with a molecular weight exclusion limit of 200,000, the molecules with a molecular weight of more than 200,000 do not pass through, while the smaller molecules pass through the membrane together with the water. During the filtration procedure no water is added, so that the volume decreases, and there is therefore an increase in the concentration of molecules with a molecular weight of more than 200,000. The product is ultrafiltered until the volume on top of the membrane is reduced to 10% of the initial volume. Two volumes of apyrogenetic, twice distilled water are added and the solution is then ultrafiltered again until the volume is reduced to ⅓. The operation is repeated two more times. The solution passed through the membrane is brought to 0.1M with sodium chloride and then precipitated with 4 volumes of ethanol at 95%. The precipitate is washed 3 times with ethanol (75%) and then vacuum dried.

The product thus obtained (Hyalastine fraction) has an average molecular weight of between 50,000 and 100,000. The HY yield is equal to 0.4% by weight of the original fresh tissue.

EXAMPLE 22

METHOD TO OBTAIN THE FRACTION HYALECTIN

The concentrated solution collected in the container on top of the ultrafiltration membrane with a molecular weight exclusion of 200,000, as in Example 21, is diluted with water until a solution containing 5 mg/ml of hyaluronic acid is obtained, as determined by quantitative analyses based on the dosage of glucuronic acid. The solution is brought to 0.1M in an aqueous sodium chloride solution and then precipitated with 4 volumes of ethanol at 95%. The precipitate is washed 3 times with ethanol (75%) and then vacuum dried.

The product thus obtained (Hyalectin fraction) has a molecular weight of between 500,000 and 730,000. This corresponds to a specific fraction of hyaluronic acid with a defined length of molecular chain of about 2,500 to 3,500 saccharide units with a high degree of purity.

The HY yield is equal to 0.2% by weight of the original fresh tissue.

METHOD B

The invention also concerns a new procedure for the preparation of hyaluronic acid salts, starting with hyaluronic acid barium salt. The new procedure regards the salts which are soluble in water and in particular the hyaluronic acid salts with active substances, in which all the carboxylic groups of hyaluronic acid may be salified or only a part of the groups are salified. In the partial salts, the remaining carboxylic groups of hyaluronic acid may be free or salified with other active substances or with alkaline metals, magnesium, aluminum, ammonium, or substituted ammonium.

The new procedure consists of preparing an aqueous solution of the barium salt of a hyaluronic acid, and adding an aqueous solution containing a number of sulfuric acid equivalents, totally or partially salified by one or more organic or inorganic bases; wherein the number of sulfuric equivalents corresponds to the number of hyaluronic acid equivalents present in the barium salt aqueous solution. The aqueous solution of hyaluronic acid salt is obtained by filtration of the separated barium sulfate. That is, by filtration of the separated barium sulfate it is possible to obtain the aqueous solution of hyaluronic acid salt from which the salt in its dry form is obtainable by concentration.

The barium salt of hyaluronic acid is not described in literature and, surprisingly, has proved to be soluble in water. It can be easily prepared by treating the not very soluble hyaluronate of cetylpyridinium with an aqueous solution of barium chloride and precipitating from the solution the hyaluronate of barium with ethanol or another suitable solvent. The hyaluronate of cetylpyridinium is an intermediate commonly used in production procedures of hyaluronic acid to separate and purify the hyaluronic acid extracted from various organic materials.

The aqueous solution, containing a number of sulfuric acid equivalents, totally or partially salified with one or more organic bases, is prepared by dissolving in water the neutral sulfates of the bases and possibly adding sulfuric acid. Should there be a solution formed of neutral sulfates of one or more organic or inorganic bases, containing a number of sulfuric equivalents corresponding to the number of hyaluronic acid equivalents present in the aqueous solution of barium salt, the end result will be a stoichiometrically neutral salt of hyaluronic acid with the bases present in the corresponding aqueous solution (sulfates). If a stoichiometrically partial salt or acid salt of hyaluronic acid be desired, sulfuric acid should be added to the aqueous solution of sulfates, or basic acid sulfates should be used.

The Method B of the invention is illustrated by the following examples.

EXAMPLE 23

METHOD OF OBTAINING A MIXTURE OF FRACTIONS HYALASTINE AND HYALECTIN IN THE FORM OF BARIUM SALTS AND WITHOUT ANY INFLAMMATORY ACTIVITY

Fresh or frozen cock's combs (3000 g) are minced in a meat mincer and then carefully homogenized in a mechanical homogenizer. The paste obtained is treated in a stainless steel container (AISI 316) or in glass with 10 volumes of anhydrous acetone. The whole is agitated for 6 hours at a speed of 50 rpm. It is left to separate for 12 hours and the acetone is discarded by syphoning. The acetone extraction is continued until the discarded acetone has reached the right degree of humidity (Karl-Fischer method). The whole is then centrifuged and vacuum dried at a suitable temperature for 5–8 hours. In this way, about 500–600 g of dry powdered cock's combs are obtained.

300 g of dry powder are exposed to enzymatic digestion with papain (0.2 g) under aqueous conditions and buffered in a phosphate buffer in the presence of a suitable quantity of cysteine hydrochloride. The resultant is agitated for 24 hours at 60 rpm, keeping the temperature constant at 60°–65° C. The whole is then cooled to 25° and Celite ® (60 g) is added, while agitation is continued for another hour. The mixture is filtered until a clear liquid is obtained. The clear liquid undergoes molecular ultrafiltration using membranes with a molecular weight exclusion limit of 30,000. Between 5 and 6 original volumes of the product are ultrafiltered, continuously adding distilled water to the ultrafiltered product. The addition of water is discontinued and ultrafiltration is continued until the volume has been reduced to ⅓ of the original volume.

The residual liquid is brought to 0.1M with the addition of barium chloride and the temperature is brought to 50° C. While agitating at 60 rpm, 45 g of cetylpyridinium chloride are added. The solution is agitated for 60 minutes and then 50 g of Celite ® are added. While agitating, the temperature of the whole is brought to 25° C. and the precipitate formed by centrifugation is collected. The precipitate is suspended in a 0.01M solution in barium chloride (5 liters) containing 0.05% of cetylpyridinium chloride. It is agitated for 60 mnutes at 50° C.; the temperature is then brought to 25° C. and the precipitate is centrifuged. The washing process is repeated 3 more times and finally the precipitate is collected in a receptacle containing 3 liters of a 0.05M solution of barium chloride containing 0.05% of cetylpyridinium chloride. The resulting suspension is agitated at 60 rpm for 60 minutes and the temperature is kept constant at 25° C. for two hours. The clear supernatant is eliminated by centrifugation.

The process is repeated several times with a solution of 0.1M barium chloride containing 0.05% of cetylpyridinium chloride. The mixture is centrifuged and the supernatant is discarded. The precipitate is dispersed in a 0.30M solution of barium chloride containing 0.05% of cetylpyridinium chloride (3 liters). The mixture is agitated and both the precipitate and the clear liquid are gathered. The precipitate undergoes extraction 3 more times, each time using 0.5 liter of the same aqueous solution.

Finally, the residue precipitate is eliminated and the clear liquids are pooled in one container. The temperature of the liquid is brought to 50° C. under constant agitation. The liquid is then brought to 0.23M with barium chloride. 1 g of cetylpyridinium chloride is added, and agitation is maintained for 12 hours. The mixture is cooled to 25° C., filtered first with Celite ® and then through a filter. It then undergoes molecular ultrafiltration once more on membranes with a molecular exclusion limit of 30,000, ultrafiltering three initial volumes with the addition of 0.33M barium chloride solution. The addition of barium chloride solution is suspended and the volume is reduced to ¼ of the original. The solution concentrated in this way is precipitated under agitation (60 rpm) at 25° C. with 3 volumes of ethanol (95%). The precipitate is gathered by centrifugation and the supernatant is discarded. The precipitate is dissolved in 1 liter of 0.1M solution of barium chloride and precipitation is repeated with 3 volumes of ethanol (95%).

The precipitate is collected and washed first three times with 75% ethanol, then with absolute ethanol (3 times), and finally with absolute acetone (3 times). The product thus obtained (fractions Hyalastine+Hyalectin) has an average molecular weight between 250,000 and 350,000. The yield of HY corresponds to 0.6% of the original fresh tissue.

EXAMPLE 24

METHOD OF OBTAINING THE FRACTION HYALASTINE IN THE FORM OF BARIUM SALT OF THE MIXTURE OBTAINED BY THE METHOD DESCRIBED IN EXAMPLE 30

The mixture obtained with the method described in Example 23 is dissolved in apyrogenic distilled water at a quantity of 10 mg of product per 1 ml of water. The solution thus obtained is subjected to molecular filtration through a membrane with a molecular exclusion limit of 200,000, following a concentration technique without the addition of water on top of the membrane. During the ultrafiltration process through membranes with a molecular exclusion limit of 200,000, the molecules with a molecular weight of more than 200,000 are detained, while the smaller molecules pass through the membrane together with the water. During the filtration process, no water is added on top of the membrane, so that the volume diminishes and consequently the concentration of molecules with a molecular weight of more than 200,000 is increased. Ultrafiltration is maintained until the volume on top of the membrane is reduced to 10% of the initial volume. Two volumes of apyrogenic distilled water are added and the whole is ultrafiltered again until the volume is reduced to ¼. The operation is repeated twice more. The solution which passes through the membrane is brought to 0.1M with barium chloride and is then precipitated with 4 volumes of 95% ethanol. The precipitate is washed 3 times with 75% ethanol and then vacuum dried. The product thus obtained (Hyalastine fraction) has an average molecular weight of between 50,000 and 100,000. The yield of HY is equal to 0.4% of fresh starting tissue.

EXAMPLE 25

METHOD OF OBTAINING HYALECTIN FRACTION IN THE FORM OF BARIUM SALT

The concentrated solution gathered in the receptacle on top of the ultrafiltration membrane with a molecular exclusion limit of 200,000, as in Example 24 is diluted with water until a solution containing 5 mg/ml of hyaluronic acid is obtained, as determined by quantitative analysis based on the glucuronic acid dosage. The solution is brought to 0.1M in barium chloride and then precipitated with 4 volumes of 95% ethanol. The precipitate is washed 3 times with 75% ethanol and then vacuum dried. The product thus obtained (Hyalectin fraction) has a molecular weight of between 500,000 and 730,000. The yield of HY is equal to 0.2% of the fresh starting tissue.

EXAMPLE 26

PREPARATION OF THE SALT OF A HYALURONIC ACID (HY) WITH STREPTOMYCIN 4.47 g of HY barium salt (10 mEq) are solubilized in 300 ml of distilled $H_2O$.

2.43 g of streptomycin sulfate (10 mEq) are solubilized in 100 ml of distilled $H_2O$, then added drop-wise under agitation to the solution of HY salt. The mixture is centrifuged for 30 minutes at 6000 rpm. The solution is separated, the precipitate is washed 2 times with 25 ml of distilled $H_2O$. The solution and the washings are pooled and then freeze dried. In the salt thus obtained, all the acid groups of hyaluronic acid are salified with the basic functions of streptomycin. Yield: 5.5 g.

Microbiological determination on *B. subtilis* (ATCC 6633) compared to standard streptomycin shows a content of 33.8% in weight of basic streptomycin, corresponding to the theoretically calculated weight. Colorimetric determination of glucuronic acid combined in the polysaccharide according to the method of Bitter et al. (Anal. Biochem. 4, 330, 1962) shows a content in weight of HY acid of 66.2% (theoretic percentage 66.0%).

EXAMPLE 27

PREPARATION OF THE SALT OF A HYALURONIC ACID (HY) WITH NAPHAZOLINE 4.47 g of the barium salt of HY with a molecular weight of 625,000 corresponding to 10 mEq of a monomeric unit are solubilized in 400 ml of distilled $H_2O$.

2.6 g of neutral naphazoline sulfate (10 mEq sulfate) are solubilized in 50 ml of distilled water and added to the solution of HY barium salt. The mixture is agitated at 5° until the barium sulfate is completely precipitated. After centrifugation the resulting solution is frozen and instantly freeze dried. Yield: 5.72 g.

In the salt thus obtained all the acid groups of HY acid are salified with naphazoline. Quantitative spectrophotometric determination compared with standard naphazoline (USP) showed a content of 35.7% in weight of basic naphazoline, corresponding to the theoretically calculated value. Colorimetric determination of the glucoronic acid combined in the polysaccharide, carried out according to the method of Bitter et al. showed a HY acid content of 64.3%.

EXAMPLE 28

PREPARATION OF THE PARTIAL SALT OF A HYALURONIC ACID (HY) WITH NAPHAZOLINE 4.47 g of the barium salt of HY with a molecular weight of 625,000 correspondint to 10 mEq of a monomeric unit are solubilized in 400 ml of distilled H₂O.

1.54 g of acid naphazoline sulfate (10 mEq sulfate) are solubilized in 50 ml bi-distilled water and added to the solution of barium salt of HY. The mixture is agitated at 5° C. until complete precipitation of the sulfate of barium. After centrifugation, the resulting solution is instantly frozen and freeze dried. Yield: 4.5 g.

In the salt thus obtained 50% of the acid groups of HY acid are salified with naphazoline and 50% are free. Quantitative spectrophotometric determination in comparison to standard naphazoline (USP) shows a content in weight of basic naphazoline which corresponds to the theoretically calculated value.

EXAMPLE 29

PREPARATION OF THE SALT OF A HYALURONIC ACID (HY) WITH PHENYLEPHRINE 2.16 g of neutral L-phenylephrine sulfate (10 mEq) are solubilized in 25 ml of distilled H₂O.

4.47 g of the barium salt of HY with a molecular weight of 820,000 corresponding to 10 mEq of a monomeric unit are solubilized in 400 ml of distilled water and added to the solution of sulfate phenylephrine. The mixture is agitated until the barium sulfate is completely precipitated. After centrifugation the resulting solution is frozen and freeze dried. In the salt obtained all the acid groups of HY are salified with phenylephrine.

U.V. spectrophotometric determination carried out by the standard addition method (USP) shows a content of 30.6% of basic phenylephrine, corresponding to the theoretically calculated value.

Colorimetric determination of the glucuronic acid combined in the polysaccharide according to the method of Bitter et al. shows an HY acid content of 69.4%.

EXAMPLE 30

PREPARATION OF THE MIXED SALT OF A HYALURONIC ACID (HY) WITH NEOMYCIN, WITH PHENYLEPHRINE AND SODIUM 7.15 g of HY barium salt with a molecular weight of 65,000 corresponding to 16 mEq of a monomeric unit are solubilized in 400 ml of distilled H₂O.

1.28 g of neomycin sulfate (8.42 mEq) are solubilized in 150 ml of distilled H₂O. 0.34 g of neutral phenylephrine sulfate (1.58 mEq) and 0.43 g of Na₂SO₄ (6 mEq) are added to the solution. The resulting solution is added to the solution of HY barium salt and, after complete precipitation of the barium sulfate, the mixture is centrifuged.

The barium sulfate is separated and the solution is frozen and freeze-dried. Yield: 7.35 g.

PHARMACOLOGICAL STUDIES

The technical effect of the new medicaments according to the present invention may be demonstrated in vivo by experiments on the rabbit eye which show their superiority as compared to the use of component (1) when administered in a conventional way. As an example, hereinafter are reported experiments carried out with hyaluronic acid salts with the following antibiotics: streptomycin, erythromycin, neomycin, gentamicin. These are the total salts in which all of the acid groups of hyaluronic acid are salified with a basic group of the antibiotic, and are described in examples 1, 2, 4 and 5. Of these, solutions in distilled water were used, having concentrations suitable to the antibiotic content, as follows:

hyaluronic acid+streptomycin (HYA1)—33.8%
hyaluronic acid+erythromycin (HYA2)—66.0%
hyaluronic acid+neomycin (HYA4)—21.2%
hyaluronic acid+gentamicin (HYA5)—20.0%

The activity of these antibiotics was compared to that given by the same antibiotics dissolved in phosphate buffer and having the same concentrations of antibiotic. The activity of the two groups of products was measured on the basis of the time necessary to suppress a dry inflammation of the rabbit eye induced by a bacterial agent. More precisely, the dry inflammation was determined in both eyes of 24 rabbits by intraocular injection of a titered suspension of one of the following bacterial groups: *Pseudomonas aeruginosa, Staphylococcus aureus, Salmonella typhi* (0.1 ml).

The various saline derivatives of the antibiotics were administered (3 drops every 6 hours) into the right eye (RE) of the rabbits, while into the left eye (LE) was instilled the corresponding quantities of the antibiotics dissolved in phosphate buffer. The treatment was begun immediately after injection of the bacterial suspension and was continued until inflammation disappeared. Both eyes of each rabbit were observed with a slit lamp. In particular the following were examined: the state of the conjuntiva and the corneal eptithelium, anterior chamber (presence of the Tyndall effect), and the state of the iris of the posterior segment of the eye. The state of the back of the eye was examined with a Goldman lens. The presence of signs of inflammation (hyperemia, exudates, cloudiness of the liquids etc.) was registered. The percentage of eyes which did not present any signs of inflammation was then calculated.

The results of the experiments are reported in Table 1, whereby it can be observed that administration of the saline derivatives according to the present invention was followed by a more rapid recovery from inflammation as compared to the administration of the corresponding antibiotics not salified with hyaluronic acid.

TABLE 1

| Effect of the administration of the derivatives HYA on recovery from dry inflammation in rabbit eye. | | | | | | | | |
|---|---|---|---|---|---|---|---|---|
| | DAYS FROM THE START OF INFLAMMATION | | | | | | | |
| TREATMENT | 1 | 2 | 3 | 4 | 5 | 6 | 7 | 8 |
| Streptomycin (6)* | 0.0 | 0.0 | 0.0 | 0.0 | 0.0 | 16.6 | 50.0 | 100.0 |
| HYA1 (6)* | 0.0 | 0.0 | 16.6 | 16.6 | 50.0 | 100.0 | 100.0 | 100.0 |
| Erythromycin (6)** | 0.0 | 0.0 | 0.0 | 0.0 | 0.0 | 0.0 | 16.6 | 33.3 |
| HYA2 (6)** | 0.0 | 0.0 | 0.0 | 0.0 | 16.6 | 16.6 | 33.3 | 50.0 |
| Neomycin (6)*** | 0.0 | 0.0 | 0.0 | 0.0 | 0.0 | 0.0 | 16.6 | 33.3 |
| HYA4 (6)*** | 0.0 | 0.0 | 0.0 | 16.6 | 16.6 | 33.3 | 33.3 | 50.0 |
| Gentamycin (6)* | 0.0 | 0.0 | 0.0 | 0.0 | 0.0 | 33.3 | 50.0 | 100.0 |
| HYA5 (6)* | 0.0 | 0.0 | 0.0 | 16.6 | 33.3 | 50.0 | 100.0 | 100.0 |

Values are expressed as percentages (number of eyes where inflammation had been relieved out of the total number of eyes treated). Between brackets are the number of eyes treated.
*Injection of *pseudomonas aeruginosa*
**Injection of *staphylococcus aureus*
***Injection of *salmonella typhi*

The technical effect of the medicaments according to the invention is further demonstrated by the following other experiments regarding the miotic, anti-inflammatory, wound healing and antimicrobial action.

I.
MIOTIC ACTIVITY OF PILOCARPINE NITRATE VEHICLED IN HYALURONIC ACID

Materials

The following materials were used as excipients for pilocarpine for the various formulations of pilocarpine nitrate:

hyaluronic acid sodium salt, Hyalastine fraction, (molecular weight about 100,000), at concentrations of 10 mg/ml and 20 mg/ml;

hyaluronic acid sodium salt, Hyalectin fraction, (molecular weight 500,000–730,000) at concentrations of 10 mg/ml and 20 mg/ml.

5% polyvinyl alcohol as ophthalmic excipient of comparison

Various formulations at 2% (collirium or gel) of pilocarpine nitrate were prepared and vehicled by adding the two different fractions of HY sodium salt at concentrations of 10 and 20 mg/ml. The following solutions were prepared:

formulation 1.—saline with pilocarpine nitrate (PiNO$_3$) (2%) used as a reference.

formulation 2.—solution of (PiNO$_3$) (2%) vehicled in 5% of polyvinyl alcohol used as a reference.

formulation 3.—solution of (PiNO$_3$) (2%) vehicled in Hyalastine fraction sodium salt (10 mg/ml).

formulation 4.—solution of (PiNO$_3$) (2%) vehicled in Hyalastine fraction sodium salt (20 mg/ml).

formulation 5.—solution of (PiNO$_3$) (2%) vehicled in Hyalectin fraction sodium salt (10 mg/ml).

formulation 6.—solution of (PiNO$_3$) (2%) vehicled in Hyalectin fraction sodium salt (20 mg/ml).

Method

Albino New Zealand rabbits were used (2–2.5 kg). The formulation to be tested was instilled in one eye of each rabbit with a microsyringe (10 mcl). The other eye was used as a reference. The diameter of the pupil was measured in all cases at suitable intervals of time Each solution was tested on at least 8 rabbits. Each eye was treated not more than three times and a rest period of at least a week was observed between each treatment.

Parameters

Measurements were made of the diameters of the pupils at various intervals to determine the miotic activity curve according to time. The following activity parameters were then calculated by miosis/time graphs:

I max = maximum difference in the diameter of the pupil between the treated eye and the reference eye Time of the maximum peak = time taken to reach the I max duration = time taken to return to basal conditions.

plateau = period of absolute miotic activity

AUC = area under the miosis/time curve

Results

The results of the studies are reported in Table 2. It is possible to see from the data from the various parameters determined by the time curve of miotic activity for all the solutions studied that the addition to hyaluronic acid at 2% of pilocarpine nitrate solutions causes an increase in the miotic activity of the drug. Indeed the bioavailability of the drug may be 2.7 times greater than that of the aqueous solution containing 2% pilocarpine nitrate (formulation 1).

It is important also to note that there is a statistically significant increase in the activity when the Hyalectin fraction of hyaluronic acid is used as a vehicle both at 10 and 20 mg/ml (formulations 5–6), compared to the pilocarpine nitrate solutions vehicled in polyvinyl alcohol (formulation 2). The use of hyaluronic acid as a vehicle is particularly interesting because the miotic activity of pilocarpine nitrate lasts longer when it is vehicled with this substance. That is, for the formulations containing hyaluronic acid the time necessary for the diameter of the pupil to return the basal conditions is more than 190 minutes (formulation 6) compared to 110 minutes for pilocarpine in saline alone (formulation 1).

TABLE 2

BIOLOGICAL ACTIVITY OF OPHTHALMIC FORMULATIONS CONTAINING PILOCARPINE NITRATE 2% VEHICLED BY HYALURONIC ACID*

| formulation No. | Vehicle | $I_{max}$, mm ($\pm$ LF 95%) | Time of max. peak min. | Duration in min. | Plateau min. | AUC, cm$^2$ ($\pm$ LF 95%) | Relative AUC |
|---|---|---|---|---|---|---|---|
| 1 | saline | 1.93 ± 0.35 | 20 | 110 | — | 117 ± 28 | 1 |
| 2 | 5% polyv. alcohol | 2.33 ± 0.28 | 20 | 140 | — | 192 ± 32 | 1.64 |
| 3 | Hyalastine (10 mg/ml) | 2.50 ± 0.42 | 20 | 120 | — | 240 ± 40 | 2.05 |
| 4 | Hyalastine (20 mg/ml) | 2.58 ± 0.38 | 30 | 150 | — | 208 ± 41 | 1.78 |
| 5 | Hyalectin (10 mg/ml) | 2.50 ± 0.38 | 15 | 170 | — | 242 ± 48 | 2.06 |
| 6 | Hyalectin (20 mg/ml) | 2.70 ± 0.38 | 20 | 190 | 45 | 320 ± 45 | 2.73 |

*Reported values represent a mean value for 8 trials

II.
MIOTIC ACTIVITY OF PILOCARPINE SALIFIED WITH HYALURONIC ACID

Materials

For the various formulations of salified pilocarpine, the following products were used:

hyaluronic acid at low molecular weight (HYALASTINE, m.w. 100,000) [HY$_1$];

hyaluronic acid sodium salt at high molecular weight (HYALECTIN, m.w. between 500,000 and 730,000) [HY$_2$-Na] at concentrations of 10 mg/ml and 20 mg/ml;

polyvinyl alcohol 5% as ophthalmic vehicle to obtain comparison formulations.

The various formulations prepared were the following:

(1) saline with pilocarpine nitrate (PiNO$_3$) 2% (used as a reference);

(2) solution of PiNO$_3$ 2% vehicled with polyvinyl alcohol 5% (used as a reference);

(3) solution of pilocarpine base/$HY_1$ acid in aqueous solution. The pilocarpine base content corresponds to 2%;

(4) solution containing pilocarpine salt/$HY_1$ acid vehicled with $HY_2$-Na 10 mg/ml. The pilocarpine base content corresponds to 2%;

(5) solution containing pilocarpine salt/$HY_1$ acid vehicled with $HY_2$-Na 20 mg/ml. The pilocarpine base content corresponds to 2%.

(6) inserts of $HY_2$-Na containing pilocarpine base salt with hyaluronic acid [$HY_1$]. The pilocarpine base corresponded to 6.25%.

Method

Albino New Zealand rabbits were used (2-2.5 kg). The solution to be tested was instilled in one eye of each of the rabbits with a microsyringe (10 ul); the other eye was used as a reference. The insert was placed in the conjunctival sac by means of suitable pincers. In all cases the pupil diameter was measured at suitable intervals. Each formulation was tested on at least 8 rabbits. Each eye was treated no more than three times; a rest period of at least a week was observed between each treatment.

Parameters

The pupil diameter was measured at various intervals of time in order to determine the miotic activity curve in time and subsequent calculation, from the miosis/time graphs, of the following activity parameters:

$I_{max}$ = maximum difference in pupil diameter between the treated eye and the reference eye;
Peak time = time taken to reach the $I_{max}$;
duration = time taken to return to basal conditions;
plateau = period of absolute miotic activity;
AUC = area under the miosis/time curve.

Results

As can be seen from Table 3, where for each solution tested, the values of the various parameters registered from the miotic activity in time curve are reported, it is possible to show how salification with hyaluronic acid of Pilocarpine at 2% causes an increase in miotic activity of the drug, whose activity can reach about 2 times that shown by aqueous solution with pilocarpine nitrate 2% (formulation 1).

A statistically significant increase in activity should also be noted when hyaluronic acid with a high molecular weight is used as a vehicle both at 10 and 20 mg/ml (formulation 4-5).

Salification with hyaluronic acid is particularly interesting also in relation to the longer duration of miotic activity of pilocarpine after vehicling with such formulations: the time taken to return to normal pupil diameter under basal conditions reaches values of 160 minutes (formulation 3) compared to 110 minutes for pilocarpine (formulation 1).

TABLE 3

| formulation No. | Biological activity parameters of the ophthalmic vehicles containing hyaluronic acid | | | | | |
|---|---|---|---|---|---|---|
| | $I_{max}$, mm (± LF 95%) | Peak time min. | Duration min. | Plateau min. | AUC, cm$^2$ (± LF 95%) | relative AUC |
| 1 | 1.93 ± 0.35 | 20 | 110 | — | 117 ± 28 | 1.00 |
| 2 | 2.33 ± 0.28 | 20 | 140 | — | 192 ± 32 | 1.64 |
| 3 | 2.25 ± 0.28 | 20 | 160 | 20 | 212 ± 32 | 1.81 |
| 4 | 2.70 ± 0.43 | 30 | 180 | 40 | 280 ± 48 | 2.39 |
| 5 | 2.80 ± 0.20 | 15 | 200 | 45 | 361 ± 40 | 3.08 |
| 6 | 3.70 ± 0.30 | 40 | 230 | — | 442 ± 70 | 3.78 |

III. STABILITY OF THE CORNEAL FILMS OF THE HYALURONIC ACID AND PILOCARPINE DERIVATIVES

The aim of the experiments was to evaluate the adhesive and filmogeneous properties of the derivatives of salification between pilocarpine and hyaluronic acid following application to the cornea of animals.

Method

The test consisted in visually evaluating the formation, stability and duration of the film formed by the formulations on the cornea. To this end sodium fluorescein was added to the ophthalmic preparations (0.1%) and the eye was examined, after instillation in UV light of 366 nm.

12 albino rabbits were used in all (New Zealand, 2-2.5 kg) of both sexes. One drop (50 ul) of each vehicle was instilled in one eye of each rabbit, keeping the other eye as control.

Solutions used 1. saline at 2% of pilocarpine nitrate ($PiNO_3$);
2. solution at 2% of $PiNO_3$, thickened with polyvinyl alcohol 5% (Wacker Chemie, PVA W 48/20);
3. solution containing pilocarpine base salt/$HY_1$ acid. The pilocarpine base content corresponds to 2%;
4. solution containing pilocarpine base salt/$HY_1$ acid vehicled with $HY_2$-Na 10 mg/ml. The pilocarpine base content corresponds to 2%;
5. solution containing pilocarpine base salt/$HY_1$ acid vehicled with $HY_2$-Na 20 mg/ml. The pilocarpine base content corresponds to 2%.

All solutions contained 0.1% of sodium fluorescein. The pH of the solutions was in all cases around 5.8.

Results

The parameters relative to the fluorescence: (a) duration of the integral corneal film, (b) duration of fluorescence (time necessary for the total disappearance of fluorescence from the eye), (c) presence of fluoroescence in the nose (time taken by the solution after application to appear at nose level), are reported in Table 4.

The derivatives of hyaluronic acid with pilocarpine produce a stable corneal film for periods of more than 2 hours. Transcorneal penetration of pilocarpine seems therefore to depend on the capacity of hyaluronic acid to vehicle the drug forming a homogeneous and stable film on the cornea.

TABLE 4

| Solution | Duration of integral film (min) | Duration of fluorescence (min) | Appearance of fluorescence in nose (min) |
|---|---|---|---|
| 1 | 30 | 100 | 2-3 |
| 2 | 80 | 150 | 10-15 |
| 3 | 100 | 150 | 5 |
| 4 | 120 | 180 | 15-20 |
| 5 | 140 | 210 | 50 |

IV.

Anti-inflammatory activity of triamcinolone vehicled in hyaluronic acid

Material

The following was used:
solution of hyaluronic acid sodium salt HYALECTIN fraction (m.w. between 500,000 and 730,00), 10 mg/ml in saline;
solution of triamcinolone phosphate (10% in saline)

Method

The experiments were carried out on male New Zealand rabbits (average weight 1.6 kg). After an adaptation period of 5 days, intraocular inflammation was induced in the animals by injection of dextran (10%, 0.1 ml) into the anterior chamber. Administration was carried out in both eyes, in conditions of local anesthetic with Novesine 4%, inserting the needle of the syringe at the edge of the cornea in the anterior chamber at a distance of 2 ml.

The test was carried out on 10 animals.

Treatment

Treatment was carried out on each animal both in the right and the left eye by installation of 3 drops 3 times a day for a total of 6 days of respectively:
solution of triamcinolone phosphate (10% in saline) in the left eye (LE);
solution of hyaluronic acid sodium salt HYALECTIN fraction (10 mg/ml)+triamcinolone phosphate (10%) in the right eye (RE).

Parameters

The anti-inflammatory effect on the reaction induced by dextran was evaluated by observation of the eye through a slit lamp at the following intervals; 0, 1 h, 3 h, 24 h, 48 h, 3 days, 4 days, 5 days, 6 days.

The following was observed at intervals:
state of the conjunctive and the cornea, for the possible presence of hyperemia, edema, and in particular the iris, normally sensitive to inflammatory processes after injection of inflammatory agents into the anterior chamber;

Tyndall effect, in which the presence of opacity of varying intensity ("nubecola") is indicative of the presence of corpuscolar (inflammatory) elements in the anterior chamber.

The results of the observations are reported according to subjective scoring between 0 and 3 in relation to the observed effect.

Results

As reported in Table 5, administration of triamcinolone proves to have an anti-inflammatory effect on the iris and causes the disappearance of opacity (Tyndall effect) in the anterior chamber. The inflammatory process evident from the 1st-3rd hour until 3-4 days gradually disappears, returning to almost normal values, with perfect clearness of the eye, in correspondence to the 6th day. On the other hand administration associated with hyaluronic acid sodium salt HYALECTIN fraction together with triamcinolone phosphate reduces intraocular inflammation observed at the above mentioned times compared to the administration of triamcinolone phosphate alone. That is, the inflammatory process in the iris and the opacity in the anterior chamber proves to be lower as soon as 24 hours later, with progressive reduction at 48 hours and total absence of inflammatory reaction from the 4th day on.

In the conjunctiva and the cornea, fundamentally no notable inflammatory reactions were observed following injection of dextran into the anterior chamber.

Thus, administration of triamcinolone phosphate together with the hyaluronic acid fraction resulted in an increase in activity of the drug, demonstrated by faster decongestion of the rabbit eye.

TABLE 5

EFFECT OF THE COMBINATION OF HYALURONIC ACID AND TRIAMCINOLONE PHOSPHATE ON DEXTRAN-INDUCED INTRAOCULAR INFLAMMATION

| | Observation times | | | | | | | | |
|---|---|---|---|---|---|---|---|---|---|
| | 0 | 1 hr | 3 hr | 24 hr | 48 hr | 3 days | 4 days | 5 days | 6 days |
| Conjunctiva | 0.0 0.0 | 0.2 0.0 | 0.0 0.0 | 0.0 0.0 | 0.0 0.0 | 0.0 0.0 | 0.0 0.0 | 0.0 0.0 | 0.0 0.0 |
| Cornea | 0.0 0.0 | 1.0 0.2 | 0.0 0.7 | 0.1 0.0 | 0.0 0.0 | 0.0 0.0 | 0.0 0.0 | 0.0 0.0 | 0.0 0.0 |
| Tyndall | 0.0 0.0 | 1.0 0.2 | 3.0 3.0 | 3.0 2.1 | 3.0 1.2 | 3.0 0.2 | 2.2 0.0 | 1.2 0.0 | 0.4 0.0 |
| Iris | 0.0 0.0 | 0.5 0.7 | 2.7 2.7 | 3.0 2.5 | 3.0 1.2 | 3.0 0.4 | 2.4 0.0 | 1.5 0.0 | 0.5 0.0 |
| | LE RE | LE RE | LE RE | LE RE | LE RE | LE RE | LE RE | LE RE | LE RE |

LE = Left eye, treated with triamcinolone phosphate
RE = Right eye, treated with triamcinolone phosphate and HYALECTIN
(each value is the mean of 7 observations on a total of 7 animals and is expressed in terms of a subjective score of 0 to 3 in relation to the gradualness of the observed effect)

V.

Healing activity of EGF vehicled in hyaluronic acid

Materials

The following were used:
formulation A—EGF (epidermal growth factor), dissolved in saline (0.5 mg/5 ml)
formulation B—hyaluronic acid sodium salt HYALASTINE fraction (m.w. 100,000) dissolved in saline (10 mg/ml).

Method

The experiments were carried out on male New Zealand albino rabbits (average weight 1.8 kg). The animals, after a period of adaptation of about 5 days, underwent epithelial lesion of the cornea in suitable conditions of local anesthetic with novesine (4%).

The lesion consisted of a monocular scarification of a circular area in the optic zone, carried out using a concave glass cylinder (0.3 mm) with a sharp edge.

Treatment

The animals were subdivided into groups, each group containing 5 animals, and they then underwent pharmacological treatment by conjunctival instillation as shown below:

| Group | Treatment |
|---|---|
| Group 1 (control) | Saline |
| Group 2 | EGF solution (formulation A) |
| Group 3 | HY sodium salt solution HYALASTINE fraction + EGF solution - combination of formulation A + formulation B in the ratio 1:1 to make formulation C. |

Treatment was effected in the right eye (RE) by conjunctival instillation of 2 drops every 8 hours for a total of 3 administrations.

Parameters

Healing of the corneal epithelium was evaluated by observation of the eye and photographic documentation with a slit lamp at various intervals after scarification: 0.8 hr, 16 hr, 24 hr, 32 hr, 40 hr, 48 hr.

Results

The ophthalmic examination 1 reported in Table 4, showed that in the controls (group 1) there was complete healing (5/5 animals) 48 hours after lesion. In the animals treated with EGF (group 2) the process is apparent as soon as 24 hours after scarification with notable efficacy (4/5 animals). In the animals treated with formulation C composed of hyaluronic acid sodium salt, HYALASTINE fraction+EGF (group 3) the healing process is complete in all the animals (5/5) as soon as 16 hours after scarification.

These results show that the use of the fraction of hyaluronic acid HYALASTINE as a vehicle for EGF enhances the healing process, encouraging a faster and more efficient healing of the corneal lesions.

TABLE 6
HEALING OF LESIONS OF THE CORNEAL EPITHELIUM

| Group | Treatment | Time after scarification (hr) | | | | |
|---|---|---|---|---|---|---|
| | | 0 | 8 | 16 | 24 | 48 |
| 1° | Saline | + | + | + | + | − |
| | | + | + | + | + | − |
| | | + | + | + | + | − |
| | | + | + | + | + | − |
| | | + | + | + | + | − |
| 2° | EGF (formulation A) | + | + | + | − | − |
| | | + | + | + | − | − |
| | | + | + | + | − | − |
| | | + | + | + | + | − |
| | | + | + | + | − | − |
| 3° | Hyaluronic Acid sodium salt + EGF (formulation C) | + | + | − | − | − |
| | | + | + | − | − | − |
| | | + | + | − | − | − |
| | | + | + | − | − | − |
| | | + | + | − | − | − |

+ = unhealed eye
− = healed eye

VI.
ANTIMICROBIAL ACTIVITY OF GENTAMICIN VEHICLED IN HYALURONIC ACID

Materials

The following were used:
Gentamicin dissolved in saline (50 mg/ml)
hyaluronic acid sodium salt, HYALECTIN fraction (2 mg/ml)

Method

Septic inflammation was induced in both eyes of 11 rabbits by intraocular injection of a titered suspension of pseudomonas aeruginosa (0.1 ml). In those rabbits showing septic inflammation, hyaluronic acid HYALECTIN fraction in combination with gentamicin was administered by instillation in the right eye, and gentamicin in a phosphate saline vehicle was administered in the left eye. The treatment (3 drops every 6 hours) was begun immediately after injection of the infective agent and was continued until disappearance of the infection. The eyes of the rabbits were observed every dat with a slit lamp.

Results

Treatment with a combination of gentamicin and hyaluronic acid resulted in the more rapid disappearance of septic infection when compared to the administration of the antibiotic alone. This conclusion is clear from the data reported in Table 7.

TABLE 7
EFFECT OF GENTAMICIN VEHICLED IN HYALURONIC ACID HYALECTIN FRACTION ON SEPTIC INTRAOCULAR INFLAMMATION

| Treatment | Days from the start of inflammation | | | | | | |
|---|---|---|---|---|---|---|---|
| | 1 | 2 | 3 | 4 | 5 | 6 | 7 |
| Gentamicin + saline as vehicle | 0.0 | 0.0 | 0.0 | 0.0 | 0.0 | 36.3 | 100 |
| Gentamicin + HA HYALECTIN fraction | 0.0 | 0.0 | 9.0+ | 72.7+ | 72.7+ | 100 | 100 |

Values are expressed as percentage of the number of eyes cured of inflammation, compared to the number of eyes treated.
+ = significative differences against phosphate vehicle (− di 0.05, T test B Fischer)

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:
1. A process for the preparation of a salt of hyaluronic acid with a pharmaceutically active substance which comprises:
    (a) combining an aqueous solution of a barium salt of hyaluronic acid with a sulfate of a pharmaceutically active substance; and
    (b) separating the precipitated barium sulfate to obtain the salt of hyaluronic acid with a pharmaceutically active substance in aqueous solution.
2. A process according to claim 1, wherein said sulfate is added in an amount such that the number of sulfate equivalents is equal to the number of hyaluronic acid equivalents, thereby producing a stoichiometrically neutral hyaluronic acid salt.

3. A process according to claim 1, wherein said sulfate is added in an amount such that the number of sulfate equivalents is less than the number of hyaluronic acid equivalents, thereby producing a partially salified hyaluronic acid salt.

4. A process according to claim 1, wherein said barium salt of hyaluronic acid is further combined with a sulfate of at least one member selected from the group consisting of an alkali or alkaline earth metal, aluminum or ammonium.

5. A process according to claim 4, wherein said sulfates are added in an amount such that the number of sulfate equivalents is equal to the number of hyaluronic acid equivalents.

6. A process according to claim 4, wherein said sulfates are added in an amount such that the number of sulfate equivalents is less than the number of hyaluronic acid equivalents.

7. A process according to claim 1, wherein said active substance is at least one member selected from erythromycin, gentamycin, neomycin, streptomycin, dihydrostreptomycin, kanamycin, amikacyn, tobramycin, aureomycin, spectinomycin, erythromycin, oleandomycin, carbomycin, spiramycin, oxytetracycline, rolitetracycline, bacitracin, polymyxin B, gramicidin, colistin, chloramphenicol, lincomycin, amphotericin B, griseofulvin, nystatin, diethylcarbamazine, mebendazol, sulfacetamide, sulfadiazine, sulfisoxazole, iodeoxyuridine, adenine arabinoside, tricarpine, metacholine, carbamylcholine, aceclidine, fisostigmine, neostigmine, demacarium, stropina, propanolol timolol, pindolol, bupranolol, atenolol, metoprolol, oxprenolol, practolol, butoxamine, sotalol, butadrine, labetalol, dexamethasone, triamcinolone, prednisolone, fluorometholone and medrison.

8. A process according to claim 1, wherein the hyaluronic acid is a molecular weight fraction having a molecular weight of between about 90–80% and 0.23% of the molecular weight of integral hyaluronic acid having a molecular weight of 13 million.

9. A process according to claim 8, wherein the hyaluronic acid fraction is substantially free of hyaluronic acid having a molecular weight less than about 30,000.

10. A process according to claim 9, wherein the molecular weight fraction has an average molecular weight of about 50,000 to about 100,000, about 500,000 to about 730,000 or about 250,000 to about 350,000.

11. A process according to claim 1, wherein said pharmaceutically active substance is a substance suitable for topical administration.

12. A process according to claim 1, wherein the active substance has ophthalmological or dermatological activity.

13. A process for the preparation of a barium salt of hyaluronic acid or a molecular weight fraction thereof which comprises
(a) treating a cetylpyridinium salt of hyaluronic acid or a molecular weight fraction thereof with an aqueous solution of barium chloride; and
(b) separating the aqueous solution and adding ethanol to thereby precipitate the barium salt of hyaluronic acid or of a molecular weight fraction thereof.

14. A process according to claim 13, wherein the hyaluronic acid fraction is substantially free of hyaluronic acid having a molecular weight less than about 30,000.

15. A process according to claim 13, wherein said molecular weight fraction has an average molecular weight of about 50,000 to about 100,000, about 500,000 to about 730,000 or about 250,000 to about 350,000.

* * * * *